United States Patent [19]

Munteanu et al.

[11] 4,428,869

[45] Jan. 31, 1984

[54] COLOGNE CONSISTING OF MICROCAPSULE SUSPENSION

[75] Inventors: Marina A. Munteanu, New York; Christine Cseko, Purchase, both of N.Y.; Edward S. Oltarzewski, Mercerville, N.J.; Jerome I. Lindauer, Hillsdale, N.J.; Donald A. Withycombe, Lincroft, N.J.

[73] Assignee: International Flavors & Fragrances Inc., New York, N.Y.

[21] Appl. No.: 294,731

[22] Filed: Aug. 20, 1981

[51] Int. Cl.³ .......................... A61K 7/46; C11B 9/00
[52] U.S. Cl. ............................................. 252/522 A
[58] Field of Search ................................... 252/522 A

[56] References Cited

U.S. PATENT DOCUMENTS

| Re. 24,899 | 11/1960 | Green | 252/316 |
|---|---|---|---|
| 2,800,457 | 7/1957 | Green et al. | 252/316 |
| 2,800,458 | 7/1957 | Green | 252/316 |
| 2,886,440 | 5/1959 | Kramer et al. | 252/316 |
| 3,920,849 | 11/1975 | Marmo et al. | 426/3 |
| 4,001,438 | 1/1977 | Marmo et al. | 426/96 |
| 4,253,473 | 3/1981 | Marmo et al. | 131/2 |
| 4,259,355 | 3/1981 | Marmo et al. | 426/5 |
| 4,311,720 | 1/1982 | Marmo et al. | 426/594 |

Primary Examiner—Helen M. S. Sneed
Attorney, Agent, or Firm—Arthur L. Liberman

[57] ABSTRACT

Described are hydro-alcohol compositions of matter including, but not limited to, colognes, after-shave lotions, after-bath preparations and splash lotions, which yield continuously high fragrance intensity release, evenly and uniformly over an extended period of time and which can be adapted to yield differing aromas from a qualitative and quantitative standpoint in a controllable manner containing a mixture of (i) a non-confined fragrance composition; (ii) one or more fragrance oils which are physically entrapped in one or more types of solid particles and (iii) a suspending agent such as hydroxypropyl cellulose, silica, xanthan gum, ethyl cellulose or combinations of the previously mentioned four substances; the non-confined fragrance substance, the entrapped fragrance oil and the suspension agent being premixed prior to the subsequent creation of the hydro-alcohol compositions of matter.

15 Claims, 14 Drawing Figures

EXAMPLE V

FIG. 8 EXAMPLE VI

EFFECT OF CONCENTRATION AND KLUCEL[R] TYPE ON VISCOSITY OF WATER SOLUTIONS.

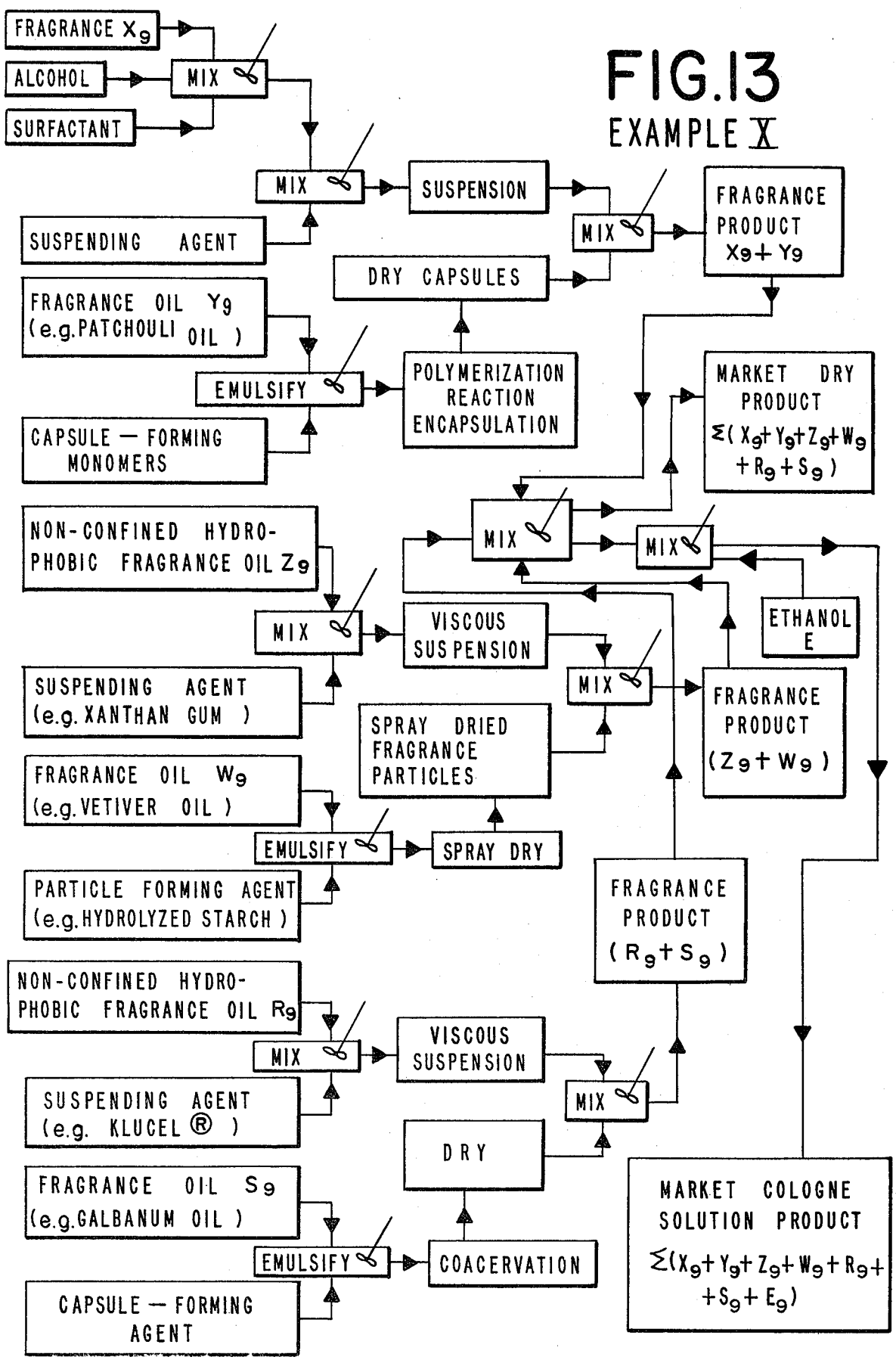

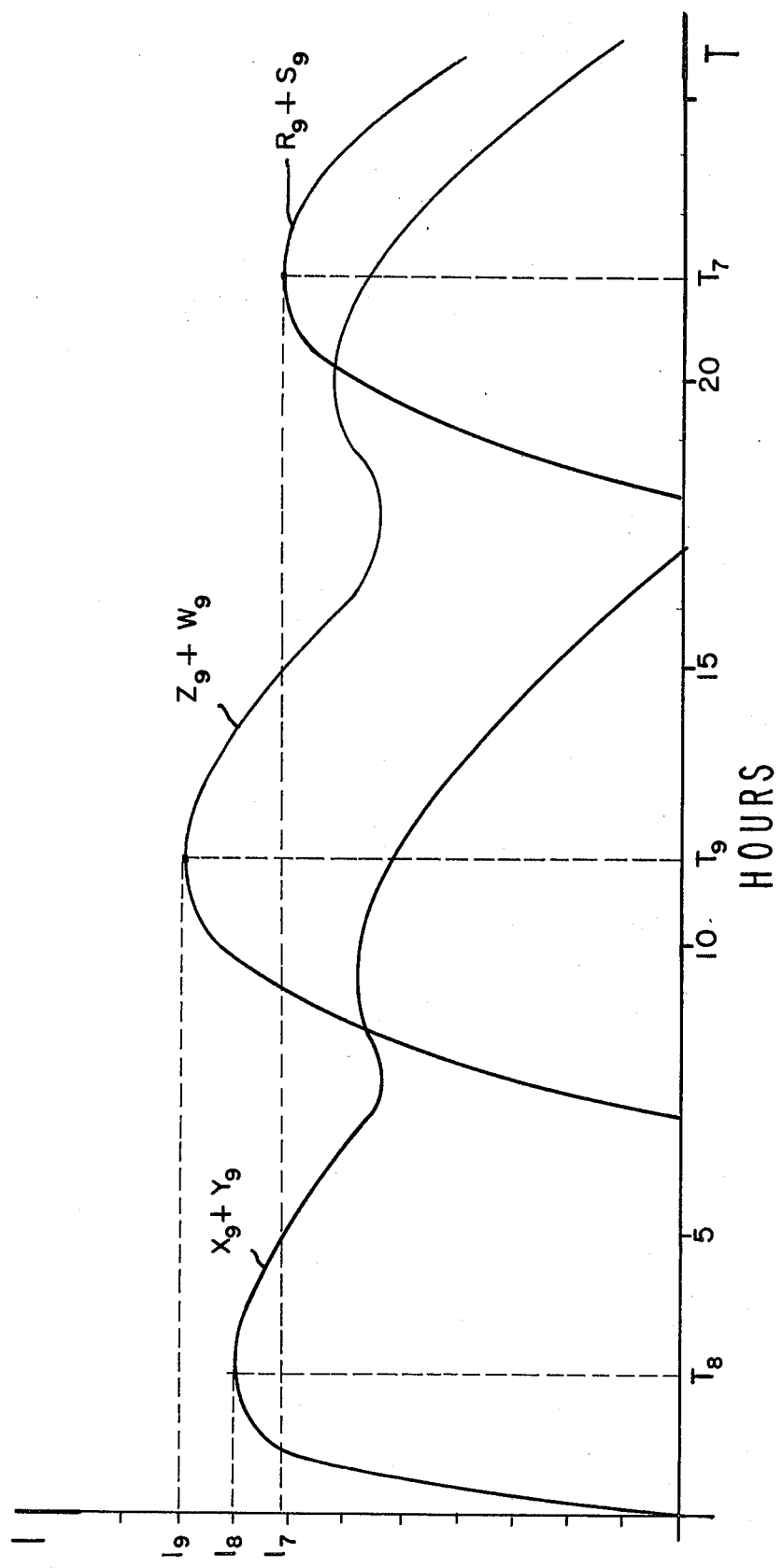
FIG.14 EXAMPLE X

COLOGNE CONSISTING OF MICROCAPSULE SUSPENSION

BACKGROUND OF THE INVENTION

This invention relates to specific fragrance compositions and specific hydro-alcohol compositions of matter. The hydro-alcohol compositions of matter when used in their proper environments, have aromas with good initial strengths which aromas are controllably released (under the normal conditions of use of the hydro-alcohol compositions of matter and under the condition of mixing with a consumable liquid, e.g., ethanol or water or combinations thereof) at a consistently high level over an extended period of time. This invention is also specially adapted for the creation of hydro-alcohol compositions of matter (e.g., colognes, after-shave lotions and after-bath splashes) which give rise to "bursts" of different fragrances from a qualitative standpoint at controllable time intervals over controllable periods of time.

There has been considerable work performed relating to fragrance substances which have a fragrance impact both initially and over an extended period of time during the consumption of the consumable material in which the fragrance is located. Problems have arisen in attempting to create such fragrance compositions for use with hydro-alcohol compositions of matter such as colognes, wherein part of the fragrance is available for immediate results whereas another part of the fragrance provides the effect gradually over extended periods of time; and further, in different manners in different controllable periods of time. Such problems include the continuous distribution of "initial impact" and "extended release" fragrance over the entire mass of the hydro-alcohol composition of matter (e.g., cologne) as well as commercial manufacture of same.

In a somewhat analogous manner, U.S. Pat. Nos. 4,253,473, 4,259,355, 4,001,438 and 3,920,849 have presented solutions to such problems where other consumable materials are concerned, e.g., smoking tobacco, hot beverages, and chewing gums. Thus, described in U.S. Pat. No. 3,920,849, are orally utilizable compositions which may be either chewing gum compositions, chewable medicinal tablets, chewing tobacco or toothpaste having, on oral intake, a high flavor intensity release evenly and uniformly over an extended oral utilization time in the mouth cavity; the orally utilizable compositions containing a non-confined flavor oil, a flavor oil which is physically entrapped in solid particles and a suspending agent such as silica, xanthan gum, ethyl cellulose and hydroxypropyl cellulose; the non-confined flavor oil, the entrapped flavor oil and the suspension agent being premixed prior to addition to either the chewing gum base, the chewing tobacco, the chewable medicinal tablet base, the toothpaste base, the smoking tobacco or the hot beverage. Neither U.S. Pat. Nos. 4,253,473, 4,259,355, 3,920,849 nor 4,001,438 discloses the use of such material for fragrancing colognes which are consumed during the standard use of such colognes, e.g., as "after-shave lotions" or standard "after-bath" colognes.

U.S. Pat. No. 1,526,039 teaches that if an essential oil or flavoring is combined with a chewing gum base in a finely divided condition, and the particles of the flavoring or oil are encased in a suitable covering so as not to contact the gum directly during manufacture, the deleterious effect of the flavoring on the gum is prevented or largely reduced. It is further stated therein that:

"When the emulsion is added to the gum base, it is thoroughly mixed therewith by the usual means employed for mixing the flavoring material with such base.

"The production of the emulsion serves to break up the essential oil into fine particles and to encase these particles in the emulsifying material, so that when the emulsion is added to the gum mass, the essential oil to a large degree is prevented from coming into direct contact with the base, and from having deleterious action thereon."

U.S. Pat. No. 2,886,440 teaches a method of preparing a chewing gum characterized by "extended flavor perception time, true flavor character, and high degree of flavor release comprising the steps of forming a spray-dried emulsion of a volatile, water-immiscible flavoring agent encapsulated within finely divided particles of gelatin, and substantially uniformly distributing said gelatin encapsulated flavoring agent within an all-enveloping mass of a chewable gum base."

The use of separate "fixed" and "unfixed" fragrance portions is also taught but there is no disclosure therein of the principle of this invention, to wit: mixing the fixed and unfixed fragrance portions with a suspension agent prior to either (i) adding to a standard cologne or after shave composition prior to use thereof or (ii) adding to a dry cologne mix formulation prior to addition of liquid thereto immediately prior to use.

U.S. Pat. No. 2,886,446 teaches a chewing gum comprising (1) smaller particles of gelatin characterized by faster liberation of flavor and (ii) larger particles of gelatin characterized by slower liberation of flavor, each of the gelatin particles containing dispersed therewithin, in dried emulsion form, discrete micro-droplets of a volatile water-immiscible flavoring agent, and an all-enveloping mass of a chewable gum base within which the particles are substantially uniformly distributed whereby the flavor is released substantially evenly and uniformly over the extended chewing time.

U.S. Pat. No. 2,886,445 teaches that:

"It is now possible to obtain a flavoring composition, particularly adapted for use in chewing gum which permits attainment of a product characterized by extended flavor perception time, true flavor character, and release of a large proportion of flavoring agent. This flavoring composition comprises finely divided particles of a dried hardened gelatin emulsion containing discrete micro-droplets of a volatile, water-immiscible flavoring agent. Preparation of the flavoring composition of this invention may be effected by encapsulating discrete micro-droplets of volatile, water-immiscible flavoring agent within finely divided particles of a dried emulsion of hardened gelatin."

U.S. Pat. No. 2,886,449 teaches:

"A chewing gum containing a flavoring composition characterized by an extended flavor perception time, true flavor character, controlled release of a large portion of flavoring agent, and reduction in amount of flavor oil required (which) may be prepared by the process comprising forming a gelatin-coacervated flavor, and substantially uniformly distributing said gelatin-coacervated flavor within an all-enveloping mass of a chewable gum base. The product chewing gum . . . comprises . . . finely divided particles of coacervated gelatin containing a water-immiscible flavoring agent therewithin and an all-enveloping mass of a chewing gum base within which the particles are substantially distributed."

The utilization of sustained release flavor containing capsules in such materials as chewing gum and medicinal tablets is also taught in British Pat. No. 1,205,764.

The use of sustained release flavor capsules in conjunction with polyethylene glycols (which are taught to be employed to desolventize the capsules) is set forth in British Pat. No. 1,318,799.

The use of hydroxypropyl cellulose contained in microcapsules especially for pressure sensitive copying paper is disclosed in Japanese Patent No. J7 9000 426 claiming a priority of U.S. Application Ser. No. 480,956 filed on June 19, 1974 and assigned to the Mead Corporation. In said Japanese Patent No. J7 9000 426, it is indicated that oil-containing microcapsules especially for pressure sensitive copying paper are prepared by (a) preparing an aqueous solution of hydroxypropyl cellulose containing reactive hydroxyl groups and having a decreasing water solubility as the temperature increases; (b) then preparing a solution of an oil soluble cross-linking agent for the hydroxypropyl cellulose in an oil; then emulsifying the oil solution in the aqueous solution to form an emulsion containing droplets of the oil solution; (c) then heating the emulsion to a temperature above the precipitation temperature of the hydroxypropyl cellulose so that hydroxypropyl cellulose precipitates over the droplets to form solid microcapsule walls and (d) finally maintaining the emulsion at this temperature until the microcapsule walls become insoluble in water and in the oil. Nothing in the Japanese Patent No. J7 9000 426 discloses the creation of a cologne composition or a powdered cologne composition wherein the fragrance thereof is controllably released during the use activity at a consistently high level over an extended period of time.

In U.S. Pat. No. 3,623,489, the formation of a shredded tobacco material having intimately admixed therewith a micro-encapsulated synthetic clove flavoring material (wherein the capsules are of such a size as to create an audible crackling sound when burned) and the incorporation thereof into smoking articles such as cigarettes and cigars is disclosed. It is further disclosed that these capsules may also contain a tobacco flavor enhancer.

U.S. Pat. No. 3,753,730 issued on Aug. 21, 1973 discloses processes for altering the flavors of particulate grain products comprising applying a composition comprising a flavoring agent, an edible cold water insoluble film former and a vehicle to a particulate grain product; drying the distributed composition to form a flavor containing film on the grain product; and then optionally distributing the coated flavored grain through a large mass of uncoated grain particles.

German Offenlegungsschrift No. 2,826,042 published on Jan. 4, 1979 discloses a condiment consisting of a lemon flavored salt prepared by mixing salt and a lemon oil powder and spraying the resulting mixture with lemon oil. More particularly, the salt is admixed with (a) from 0.1 up to 0.5 weight percent of salt of a terpene-free lemon oil bonded to a powdery carrier and (b) terpene-free liquid lemon oil. The condiment is prepared by mixing the dry salt with component (a), spraying the mixture with component (b) and mixing through a screw conveyor.

Hydroxypropyl cellulose itself is described in particular in three publications:
  a. Hercules/Klucel ®/hydroxypropyl cellulose published by Hercules Incorporated of Wilmington, Del.;
  b. Klug, Vol. 24, No. 51, Food Technology, January, 1970, page 51 entitled "Functional Helpmate to Development . . . Hydroxypropyl Cellulose/a New Water Soluble Cellulose Polymer"; and
  c. U.S. Pat. No. 3,278,521, issued on Oct. 11, 1966 entitled: "Hydroxypropyl Cellulose and Process"-/Inventor: Klug.

However, the prior art does not set forth commercially feasible processes for creating cologne compositions containing an aromatizing composition which provides instantaneous evenly distributed aroma release, extended, continuous, non-interrupted fragrance perception time periods and, at the same time, provides during the cologne use activity, extended constant fragrance impact which is provided by our invention.

The use of "spray dried fragrances" is not, however, new to the art. "Spray dried fragrances" are known as taught in the following prior art:
  a. Miles et al, J. Soc. Cosmet. Chem., 22, 655–666 (Sept. 17, 1971) ["Encapsulated Perfumes in Aerosol Products"]
  b. Brenner et al, U.S. Pat. No. 3,971,852 issued July 27, 1976 (Process of Encapsulating an Oil and Product Produced Thereby).

The Miles et al article discloses an apparently stable spray dried encapsulated fragrance which may be formulated into aerosols. It is indicated that when sprayed on a surface under both in vivo and in vitro conditions gradually release fragrance upon exposure to moisture. It is further shown by Miles et al that the release rate can be varied according to the liquid vehicle and that it varies with the individual test subject and to the stimuli to which he or she is exposed.

The Brenner et al, U.S. Pat. No. 3,971,852 discloses interalia perfume compositions, preferably in particulate form, comprising a cellular matrix having oil in the cells thereof in which the matrix comprises a polysaccharide and a polyhydroxy compound in such proportions that the oil may constitute up to 80% by volume so stably held in the cells that the extractable oil is not substantially in excess of 5%. The polysaccharides are indicated to be natural gums such as gum arabic, starch derivatives and dextrinized and hydrolyzed starches. It is further indicated that the polyhydroxy compounds may be alcohols, lactones, monoethers, plant-type sugars and acetals.

Nothing in either of the Brenner et al U.S. Pat. No. 3,971,852 or the Miles et al article infers the concept of our invention.

BRIEF DESCRIPTION OF THE DRAWINGS

FIG. 13 sets forth a block diagram flow sheet indicating the preparation of the fragranced solid cologne and liquid cologne of our invention as more fully described in Example X, identified by the trademark "TROIS COTES DU FORCE! ™" since three distinct fragrances are evolved over a period of 24 hours commencing with use of the cologne.

FIG. 14 is a graph of time (on the X axis) vs. intensity of aroma evolved from user (scale 1-10) on the Y axis for the performance of the fragranced cologne powder over a period of 24 hours beginning with use in alcoholic solution.

OBJECTS OF THE INVENTION

Figure 1:
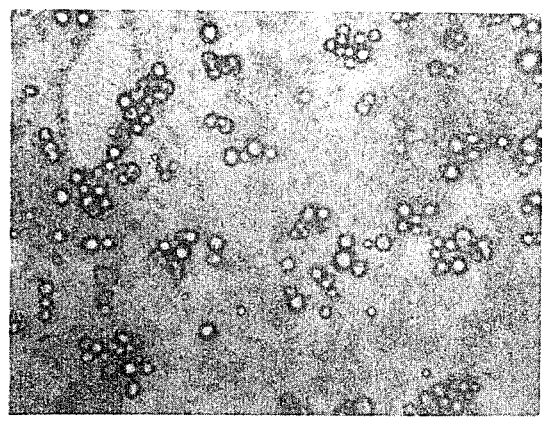
FIG. 1 is a photomicrograph of the cologne suspension produced according to Example I (200X magnification).

It is an object of this invention to provide a hydro-alcohol composition of matter (e.g., cologne) containing a perfume composition characterized by (i) an almost instantaneous aroma perception prior to the use and on use and (ii) over an extended period of time on use, controlled, constant and continuous non-interrupted, high impact fragrance release.

A second object of this invention is to increase the total amount of aroma release during the use of the hydro-alcohol composition of matter (e.g., cologne) containing the herein described aroma composition.

A third object of this invention is to provide a dry hydro-alcohol composition of matter (e.g., "dry cologne") which on admixing with a consumable liquid yields a high aroma intensity release substantially evenly and uniformly over an extended use period.

Further objects of this invention will be apparent to those skilled in the art from the following detailed description of the invention.

THE INVENTION

This invention relates to fragrance compositions for use in "dry hydro-alcohol compositions of matter" (e.g., "dry colognes") which are, in turn, used in splash-on colognes, after-bath splashes, after-shave lotions and the like. The hydro-alcohol compositions of matter (e.g., colognes or dry colognes) have fragrances with good, evenly distributed initial strength and this fragrance or series of fragrances, as the case may be, is controllably released with continuous non-interrupted high fragrance impact over an extended period of time during the use of the hydro-alcohol composition of matter (e.g., splash-on, after-shave or cologne formula); and to processes for preparing such fragrancing compositions.

The invention also relates to perfume compositions which tend to yield various (one or more) perfume aroma profiles at controlled intensities over given periods of time for discrete time intervals.

The hydro-alcohol composition of matter (e.g., cologne) contains a mixture of (i) a non-confined fragrance oil (emulsified or non-emulsified or both); (ii) a fragrance oil which is physically entrapped in solid non-toxic particles and (iii) a suspending agent such as hydroxypropyl cellulose, ethyl cellulose, silica or xanthan gum; the non-confined oil, the fragrance oil which is physically entrapped in solid particles and suspending agent being premixed prior to addition to a carrier liquid for use or for marketing.

As used herein with regard to fragrances, the terms "alter" and "modified" in their various forms mean "supplying or imparting aroma character or note to otherwise bland colognes or perfume compositions or augmenting the existing aroma characteristic where a natural aroma is deficient in some regard or supplementing the existing aroma impression to modify its quality, character or taste."

As used herein the term "enhance" is intended to mean the intensification (without change in kind or quality of aroma) of one or more aroma nuances present in the organoleptic impression of a synthetic or natural essential oil.

Our invention thus provides (i) an organoleptically improved perfume product and additives therefor as well as (ii) methods of making same which overcome specific problems heretofore encountered in which the improved aromatized compositions have an aroma with good initial strength and have one or more aromas which are controllably released during the use activity of the hydro-alcohol compositions of matter (e.g., colognes) at a consistently high level over an extended period of time prior to actual use and on use thereof.

Our invention further provides improved aromatized additives (e.g., perfume compositions and colognes) and methods whereby various nuances may be imparted to colognes and other perfumed products and may be readily varied and controlled to produce the desired uniform (or uniform for discrete periods of time) characteristics wherein one or more of the aromas have good initial strength and wherein one or more of the aromas is controllably released during the use activity at a consistently high level over one or more extended periods of time.

Thus, it has been found that it is now possible to obtain a dry hydro-alcohol composition of matter (e.g., "dry cologne") or a hydro-alcohol composition of matter in solution (e.g., after-bath splash, cologne or after-shave lotion) containing one or more fragrance compositions which provide almost (i) instantaneous fragrance release on use thereof in extended high intensity, (ii) constant fragrance perception time during use, (iii) true fragrance character and (iv) controlled release of the major proportion of fragrancing agent initially present in the fragrance composition. It has been further found that it is now possible to obtain the impact of two, three or more different fragrances at different periods of time over the course of the day and night by the user. The quantity of fragrance evolved and the quality of fragrance evolved over given periods of time are functions of the ratios of the particular ingredients utilized in the dry cologne as explained in more detail, infra.

The fragrance compositions of our invention consist essentially of one or a combination of the following suspensions of entrapped fragrance in a solid in a liquid fragrance medium whereby no settling of the entrapped fragrance occurs in the liquid medium which is also a fragrance at least compatible with the entrapped fragrance if not the same as the entrapped fragrance.

I. Specifically Embodied in Examples I, II, VI and VIII

Figure 12:
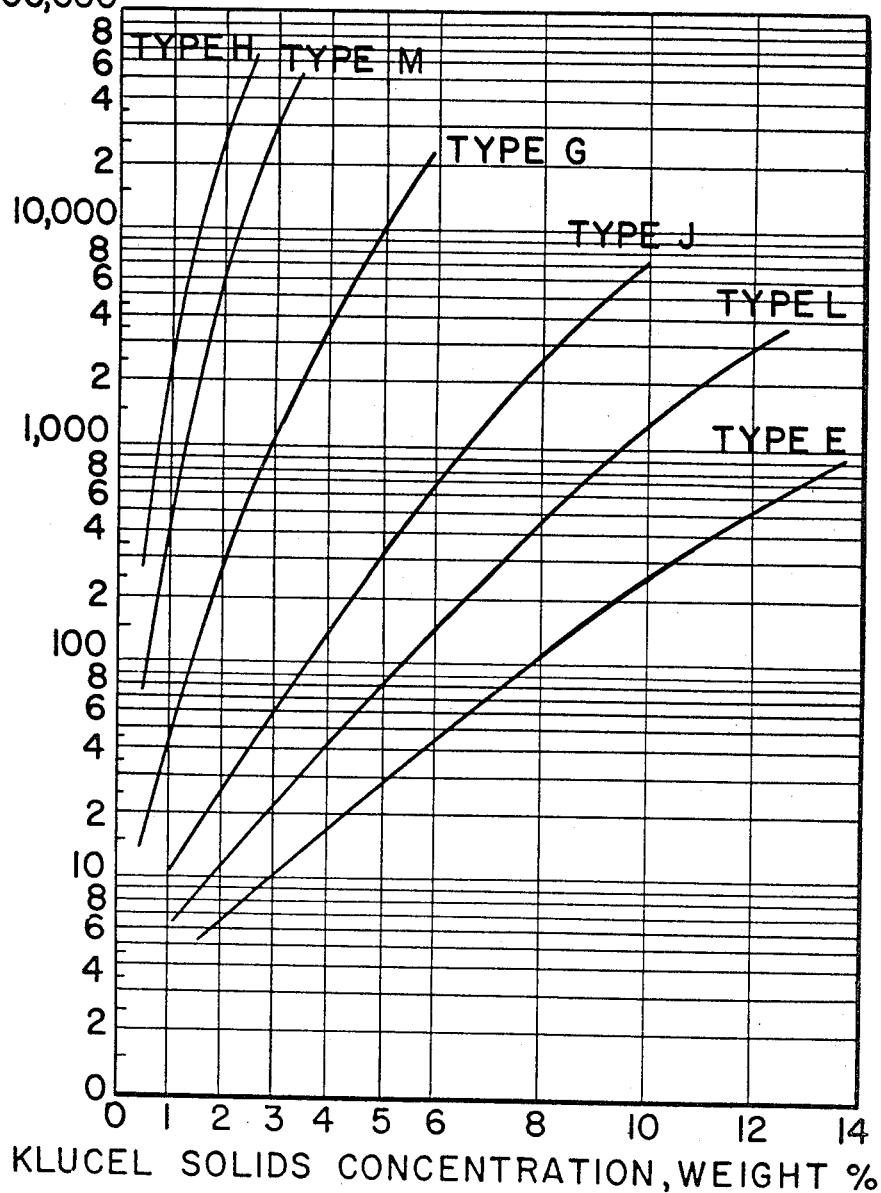
FIG. 12 sets forth a graph indicating the Klucel® brand of hydroxypropyl cellulose solids concentration (weight percent) vs. Brookfield viscosity at 25° C. in centipoises for types E, L, J, G, M and H Klucel® hydroxypropyl cellulose materials. Thus, FIG. 12 indicates the effect of concentration of Klucel®-type on the viscosity of water solutions.

A. From about 1 part by weight up to about 10 parts by weight of a non-confined fragrance in alcoholic solution which alcoholic solution contains a surfactant;

b. From about 0.1 parts by weight up to about 10 parts by weight of a solid suspending agent which may or may not be hydrated with water, selected from the group consisting of clays, e.g., smectite clay, hydroxypropyl cellulose having a molecular weight of from about 50,000 up to about 800,000, a structure as follows:

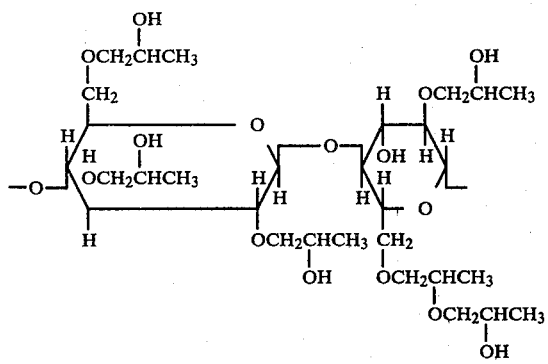

having a particle size such that 95% of the particles pass through 30 mesh screens and 99% of the particles pass through 20 mesh screens and having a viscosity defined according to FIG. 12; or colloidal silica, xanthan gum or ethyl cellulose having a particle size of from about 0.004 up to about 0.130 microns, a surface area of from about 100 up to about 500 m² per gram and a density of from about 1.0 up to about 4.0 pounds per cubic foot;

c. From about 2 up to about 10 parts by weight of an entrapped fragrance oil which is releasable either (i) hydrolytically (as a result of contact with excreted sweat) or (ii) by means of the application of mechanical pressure (for example as a result of rubbing or washing and/or normal contact between the skin and clothing article), physically entrapped in a solid material, said solid material having a particle size of from about 3 microns up to about 400 microns, said physically entrapped fragrance oil being organoleptically compatible with the non-confined fragrance oil of "a".

II. Specific Embodiments of Examples III, IV, V and IX a. From about 1 up to about 10 parts by weight of a non-confined hydrophobic fragrance oil;

b. From about 0.1 up to about 10 parts by weight of a solid suspending agent selected from the group consisting of hydroxypropyl cellulose having a molecular weight of from about 50,000 up to about 800,000, a structure as follows:

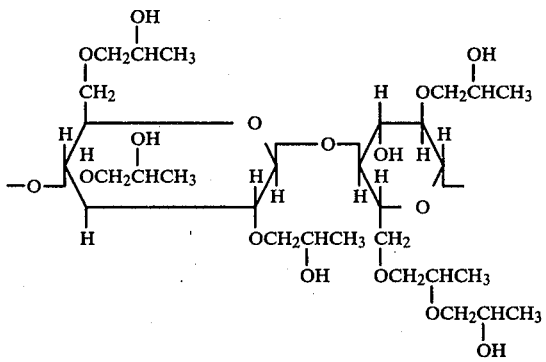

having a particle size such that 95% of particles are passed through 30 mesh screens and 99% of the particles are passed through 20% mesh screens and having a viscosity defined according to FIG. 12; or colloidal silica; or xanthan gum; or ethyl cellulose having a particle size of from about 0.004 up to about 0.130 microns, a surface area of from about 100 up to about 500 m² per gram and a density of from about 1.0 up to about 4.0 pounds per cubic foot;

c. From about 2 up to about 10 parts by weight of an entrapped fragrance oil releasable either (i) hydrolytically (as a result of contact with excreted sweat) or (ii) by means of the application of mechanical pressure (for example, as a result of rubbing or washing and/or normal contact between the skin and clothing articles), physically entrapped in a solid material, said solid material having a particle size of from about 3 microns up to about 400 microns, said physically entrapped fragrance oil being organoleptically compatible with the non-confined hydrophobic fragrance oil.

III. Embodiment of Example VII a. From about 1 part up to about 10 parts by weight of a non-confined hydrophobic first fragrance oil;

b. From about 0.1 up to about 10 parts by weight of a solid suspending agent for suspending such first fragrance oil selected from the group consisting of hydroxypropyl cellulose having a molecular weight of from about 50,000 up to about 800,000 a structure as follows:

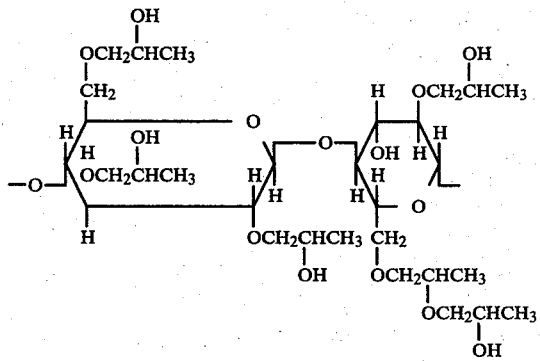

having a particle size such that 95% of the particles pass through 30 mesh screens and 99% of the particles pass through 20 mesh screens and having a viscosity defined according to FIG. 12; or colloidal silica; xanthan gum or ethyl cellulose having a particle size of from about 0.004 up to about 0.130 microns, a surface area of from about 100 up to about 500 square meters per gram and a density of from about 1.0 up to about 4.0 pounds per cubic foot;

c. For the non-confined hydrophobic first fragrance oil, from about 2 up to about 10 parts by weight of an entrapped fragrance oil releasable either (i) hydrolytically (as a result of contact with excreted sweat) or (ii) by means of application of mechanical pressure (for example, as a result of rubbing, or washing and/or normal contact between the skin and clothing article), physically entrapped in a solid material, said solid material having a particle size of from about 3 microns up to about 400 microns, said physically entrapped fragrance oil being organoleptically compatible with the non-confined hydrophobic first fragrance oil as well as the confined and non-confined fragrance materials as set forth infra in "d", "e", and "f";

d. From about 1 part by weight up to about 10 parts by weight of a second fragrance oil, which is compatible from an organoleptic standpoint with said first fragrance oil and which is compatible with said entrapped fragrance oil, in an alcoholic solution with a surfactant material. The surfactant material may be, and is preferred to be, a nonionic surface active material such as a sucrose ester, having the generic structure:

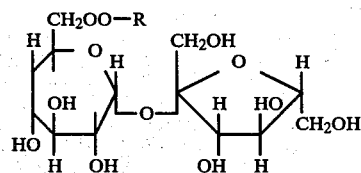

wherein R represents an alkyl group of a fatty acid.

c. For the non-confined second fragrance oil, from about 0.1 up to about 10 parts by weight of a solid suspending agent or a suspending agent combined with water which may be, for example, smectite clay or another type of clay defined as "Ben-A-Gel ®" which is a highly beneficiated smectite clay having a specific gravity of 2.5, a density of 20.9 pounds per gallon and a bulking value of 0.0479 gallons per pound; or hydroxypropyl cellulose having a molecular weight of from about 50,000 up to about 800,000, a structure as follows:

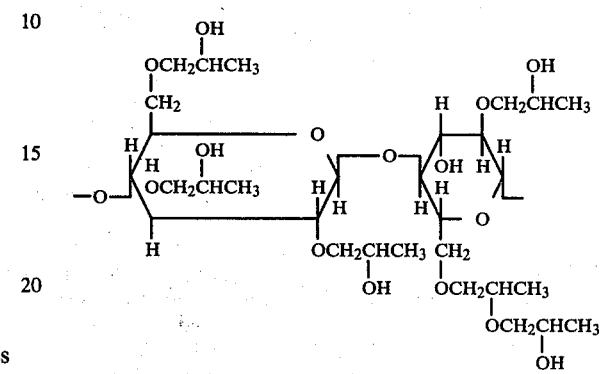

having a particle size such that 95% of the particles are passed through 30 mesh screens and 99% of the particles are passed through 20 mesh screens and having a viscosity defined according to FIG. 12; or colloidal silica, xanthan gum or ethyl cellulose having a particle size of from about 0.004 up to about 0.130 microns, a surface area of from about 100 up to about 500 m² per gram and a density of from about 1.0 up to about 4.0 pound per cubic foot;

f. For the non-confined second fragrance oil, from about 2 up to about 10 parts by weight of an entrapped fragrance oil, releasable either (i) hydrolytically (as a result of contact with excreted sweat) or (ii) by means of application of mechanical pressure (for example as a result of rubbing or washing and/or normal contact between the skin and clothing articles), physically entrapped in a solid material, said solid material having a particle size of from about 5 microns up to about 400 microns, said physically entrapped fragrance oil being organoleptically compatible with the fragrance oils of "a", "b", "c", "d" and "e", supra.

IV. Specific Embodiments as Exemplified by Example

X a. From about 2 up to about 10 parts by weight of a first non-confined hydrophobic fragrance oil;

b. From about 0.1 up to about 10 parts by weight of a solid suspending agent for the fragrance oil in "a" selected from the group consisting of finely divided clay, (e.g., attapulgite clay), hydroxypropyl cellulose having a molecular weight of from about 50,000 up to about 800,000, a structure as follows:

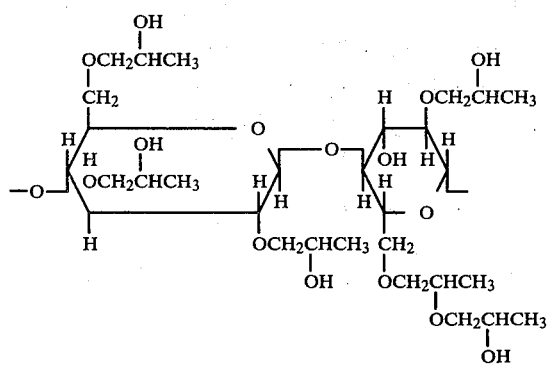

having a particle size such that 95% of the particles are passed through 30 mesh screens and 99% of the particles are passed through 20 mesh screens and having a viscosity defined according to FIG. 12; or colloidal silica, xanthan gum or ethyl cellulose having particle sizes of from about 0.004 up to about 0.130 microns, a surface area of from about 100 up to about 500 m² per gram and a density of from about 1.0 up to about 4.0 pounds per cubic foot;

c. From about 2 up to about 10 parts by weight of an entrapped fragrance oil releasable either (i) hydrolytically (as a result of contact with excreted sweat) or (ii) by means of application of mechanical pressure (for example, as a result of rubbing or washing and/or normal contact between the skin and clothing articles), compatible with the fragrance oil in "a", physically entrapped in a solid material, said solid material having a particle size of from about 5 microns up to about 400 microns, said physically entrapped fragrance oil being organoleptically with the non-confined hydrophobic flavor oil of "a";

d. From about 2 up to about 10 parts by weight of a second non-confined hydrophobic fragrance oil different from that set forth in "a" herein;

e. From about 0.1 up to about 10 parts by weight of a solid suspending agent for the fragrance oil of "d" selected from the group consisting of attapulgite clay, hydroxypropyl cellulose having a molecular weight of from about 50,000 up to about 800,000, a structure as follows:

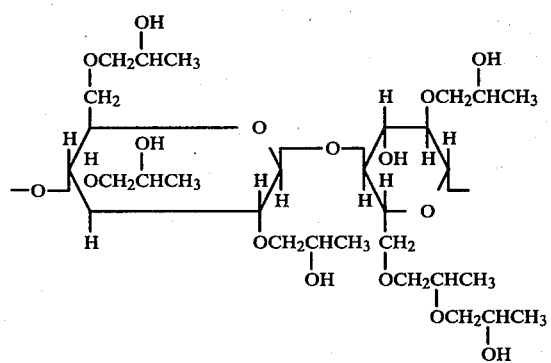

having a particle size such that 95% of the particles are passed through 30 mesh screens and 99% of the particles are passed through 20 mesh screens and having a viscosity defined according to FIG. 12; or colloidal silica, xanthan gum or ethyl cellulose having particle sizes of from about 0.004 up to about 0.130 microns, a surface area of from about 100 up to about 500 square meters per gram and a density of from about 1.0 up to about 4.0 pounds per cubic foot;

f. From about 2 up to about 10 parts by weight of an entrapped fragrance oil releasable either (i) hydrolytically (as a result of contact with excreted sweat) or (ii) by means of application of mechanical pressure (for example, as a result of rubbing or washing and/or normal contact between the skin and clothing articles), compatible with the fragrance oil of "d", physically entrapped in a solid material, said solid material having a particle size of from about 5 microns up to about 400 microns, said physically entrapped fragrance oil being organoleptically compatible with said non-confined hydrophobic fragrance oil "e" as well as "a";

g. From about 2 up to about 10 parts by weight of a third non-confined fragrance oil further mixed with an alcohol such as ethyl alcohol and a surfactant;

h. From about 0.1 up to about 10 parts by weight of a solid suspending agent for the fragrance mixture "g" selected from the group consisting of a finely divided clay e.g., attapulgite clay, or hydroxypropyl cellulose having a molecular weight of from about 50,000 up to about 800,000, a structure as follows:

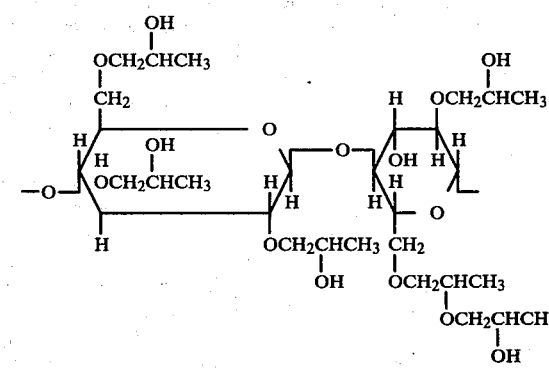

having a particle size such that 95% of the particles are passed through 30 mesh screens and 99% of the particles are passed through 20 mesh screens and having a viscosity defined according to FIG. 12; or colloidal silica; or xanthan gum; or ethyl cellulose having a particle size of from about 0.004 up to about 0.130 microns, a surface area of from about 100 up to about 500 m² per gram and a density of from about 1.0 up to about 4.0 pounds per cubic foot;

j. From about 2 up to about 10 parts by weight of an entrapped fragrance oil releasable either (i) hydrolytically (as a result of contact with excreted sweat) or (ii) by means of application of mechanical pressure (for example, as a result of rubbing or washing and/or normal contact between the skin and clothing articles), physically entrapped in a solid material, said solid material being capable of being broken down over a period of time as a result of the normal use of colognes, said solid material having a particle size of from about 5 microns up to about 400 microns, said physically entrapped fragrance oil being organoleptically compatible with the non-confined fragrance oils and fragrance oil solutions of "a", "d" and "g" as well as the confined fragrance oils of "c" and "f".

Preparation of the fragrance compositions employed in the dry hydro-alcohol compositions of matter (e.g., dry after-bath splashes, dry after-shave lotions and dry colognes) or in the liquid hydro-alcohol compositions of matter (e.g., colognes, after-bath splashes and after-shave lotions) solutions or emulsions of our invention may be effected in the alternative by:

I. As Specifically Embodied in FIGS. 3, 8 and 10

First preparing a mixture of fragrance oil, alcohol and surfactant. The range of ratios of fragrance: alcohol may vary from about 1:5 up to about 1:40 with a preferred ratio (weight:weight) of 1:10. The ratio range of fragrance:surfactant may vary from about 1:2 up to about 3:1 with a preferred ratio of 2 parts by weight of fragrance:1 part by weight of surfactant. The ratio range of alcohol:surfactant may vary from about 10:1 up to about 30:1 with a preferred ratio of alcohol:surfactant being about 20:1 (weight:weight). The type of alcohol used which is non-toxic, e.g. ethyl alcohol or isopropyl alcohol, preferably ethyl alcohol. The type of surfactant used is preferred to be a nonionic surfact active material although anionic, cationic or zwitterionic surface active materials are usable. Preferred in the group of nonionic surface active materials for the purposes of our invention are sucrose esters produced by the reaction of sucrose with tallow fatty acids having the generic structure:

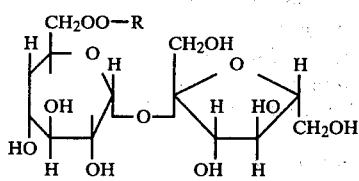

wherein R is a fatty acid alkyl group. Specific examples of such sucrose esters are "CRODESTA ®F-10, F-20, F-50, F-70, F-110, F-140 and F-150" manufactured by Croda Incorporated of 51 Madison Avenue, New York, N.Y. 10010. The properties of these esters are as follows:

| CRODESTA ® | Melting Point | Percent Monoester | HLB Value |
|---|---|---|---|
| F-10 | 64° C. | 3.0 | 3.0 max. |
| F-20 | 74° C. | 10.0 | 3.0 |
| F-50 | 74-78° C. | 29.0 | 6.5 |
| F-70 | 72-76° C. | 30.4 | 7.5 |
| F110 | 72-78° C. | 51.9 | 12.0 |
| F-140 | 70-76° C. | 57.2 | 13.0 |
| F-160 | 70-74° C. | 75.2 | 14.5 |

Additives to the fragrance:alcohol:surfactant mixture are preferred but not necessary for stabilization purposes. Such agents are, for example, methyl paraben. The resulting mixture is then admixed with from about 1.0 part by weight up to about 2 parts by weight of a suspending agent which may be a mixture of finely divided clay and water, e.g., smectite clay (Ben-A-Gel ®EW manufactured by N L Industries, Inc., P.O. Box 700, Hightstown, N.J. 08520) which is described as a highly beneficiated smectite clay having a specific gravity of 2.5, a density of 20.9 pounds per gallon and a bulking value in gallons per pound of 0.0479, or hydroxypropyl cellulose having a molecular weight of from about 50,000 up to about 800,000, a structure as follows:

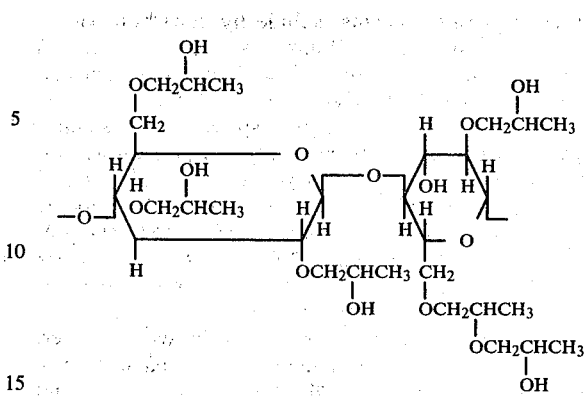

having a particle size such that 95% of the particles are passed through 30 mesh screens and 99% of the particles are passed through 20 mesh screens and having a viscosity defined according to FIG. 12; or colloidal silica, e.g., Cab-O-Sil ®M-5 brand of silica produced by the Cabot Corporation of 125 High Street, Boston, Mass. 02110 having a surface area of 200 $m^2$ per gram, a nominal particle size of 0.012 microns and a density of 2.3 pounds per cubic foot; xanthan gum and ethyl cellulose, said silica, xanthan gum and ethyl cellulose having particle sizes of from about 0.004 up to about 0.130 microns, a surface area of from about 100 up to about 500 $m^2$ per gram and a density of from about 1.0 up to about 4.0 pounds per cubic foot thereby forming a first suspension; and then:

Admixing the first suspension with from about 2 up to about 10 parts by weight of an entrapped fragrance oil releasable either (i) hydrolytically (as a result of contact with excreted sweat) or (ii) by means of application of mechanical pressure (for example as a result of rubbing or washing and/or normal contact between the skin and clothing articles), physically entrapped in a solid material, said solid material having a particle size of from about 5 microns up to about 400 microns thereby forming a second suspension, said physically entrapped fragrance oil being organoleptically compatible with the non-confined fragrance oil which is in admixture with the alcohol and the surfactant whereby the physically entrapped materials may be produced by one of the following techniques:

a. particles having a cellular matrix having the fragrance oil in the cells thereof in which the matrix comprises polysaccharide and polyhydroxy compounds in such proportions that the fragrance may constitute up to 80% by volume so stably held in the cells that the extractable perfume oil is not substantially in excess of 5% accomplished according to the procedure of U.S. Pat. No. 3,971,852 issued on July 27, 1976 (the disclosure of which is incorporated herein by reference);

b. microcapsules prepared by means of coacervation according to the process of U.S. Pat. Nos. 2,800,457; 2,800,458; 3,041,289 and 3,533,958 the disclosures of which are incorporated by reference herein;

c. microcapsules prepared by inter-phase polymerization around perfume oil microdroplets according to the process of U.S. Pat. Nos. 3,615,972 (suspension-type polymerization); 3,516,941; and 3,423,489, the disclosures of which are incorporated herein by reference.

Other entrapment agents include hydrocarbon waxes, solid surfactants (e.g., "Pluronics®"), KLUCEL® hydroxypropyl cellulose (also used as suspension agents) and mannitol-polyvinyl alcohol polymer.

In addition to the foregoing suspension agents, additional suspension agents, polymeric suspension agents, SGP® absorbent polymers produced by the Henkel Corporation of 4620 West 77th Street, Minneapolis, Minn. 55435 is operable. Examples of the "SGP®" polymers" are SGP® polymer 502S and SGP® polymer 147. The ratio of SGP® polymer to water usable in our invention may vary from 0.2 parts polymer:50 parts water up to 0.5 parts polymer:50 parts by weight water.

Additional suspension agents are defined in "Drug and Cosmetic Industry", May 1981, pages 39-42 and "Drug and Cosmetic Industry", June 1981, pages 52, 54, 56, 102, 103, 104 and 105 (articles by Alma J. Scheer). The suspension agents set forth in the Drug and Cosmetic Industry articles are:

a. microcrystalline cellulose
b. carrageenan
c. propylene glycol alginate
d. sodium alginate
e. methyl cellulose
f. sodium carboxymethyl cellulose (e.g., Hercules cellulose gum manufactured by Hercules, Inc., 910 Market Street, Wilmington, Del.)
g. Veegum (manufactured by R. T. Vanderbilt Company of 30 Winfield Street, Norwalk, Conn.) [a natural inorganic complex colloidal magnesium aluminum silicate]

It is noteworthy that the carboxymethyl cellulose and sodium carboxymethyl cellulose also act as stabilizers thereby obviating the necessity for an additional stabilizer in the system.

Subsequent to the admixing of the first suspension with the entrapped fragrance oil which is releasable either (i) hydrolytically (as a result of contact with excreted sweat) or (ii) by means of application of mechanical pressure (for example, as a result of rubbing or washing and/or normal contact between the skin and clothing articles), the resulting material may be marketed "as is" in the form of a thixotropic paste or dried as a powder and marketed or combined with ethanol and water and marketed as a hydro-alcohol composition of matter (e.g., cologne) suspension. The remarkable quality of the hydro-alcohol composition of matter (e.g., cologne) suspensions of our invention are that substantially no settling occurs and that the hydro-alcohol composition of matter suspensions are quite stable.

II. Processes Carrying out Embodiments as Set Forth in FIGS. 4, 5, 6 and 11

Preparation of the fragrance compositions employed in the hydro-alcohol compositions of matter (e.g., cologne) of this aspect of our invention may be effected by:

1. Admixing
   a. From about 1 up to about 10 parts by weight of a non-confined hydrophobic fragrance oil, and
   b. From about 0.1 up to about 10 parts by weight of a solid or viscous liquid suspending agent selected from the group consisting of an SGP® polymer solution (manufactured by the Henkel Corporation of Minneapolis, Minn.); a colloidal suspension of smectite clay (e.g., Ben-A-Gel® manufactured by N L Industries, Inc. of Hightstown, N.J.); hydroxypropyl cellulose having a molecular weight of from about 50,000 up to about 800,000 having the structure:

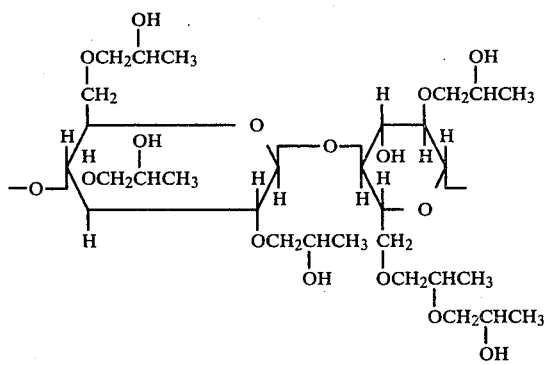

having a particle size such that 95% of the particles are passed through 30 mesh screens and 99% of the particles are passed through 20 mesh screens; having a viscosity defined according to FIG. 12; and colloidal silica, xanthan gum and ethyl cellulose having a particle size of from about 0.004 up to about 0.130 microns, a surface area of from about 100 up to about 500 $m^2$ per gram and a density of from about 1.0 up to about 4.0 pounds per cubic foot thereby forming a first suspension and then 2. Admixing the first suspension with from about 2 up to about 10 parts by weight of an entrapped fragrance oil which is physically in a solid material and which is releasable either (i) hydrolytically (as a result of contact with excreted sweat) or (ii) by means of application of mechanical pressure (for example, as a result of rubbing or washing and/or normal contact between the skin and worn clothing articles), said solid material having a particle size of from about 3 microns up to about 400 microns thereby forming a second suspension, said physically entrapped fragrance oil being organoleptically compatible with the non-confined hydrophobic fragrance oil, said solid particles being produced according to any number of processes thusly:

a. Suspension polymerization as defined according to U.S. Pat. No. 3,615,972, the disclosure of which is incorporated herein by reference;
b. Compositions in particulate form comprising a cellular matrix having the perfume oil in the cells thereof in which the matrix comprises polysaccharide and polyhydroxy compounds in such proportions that the perfume oil may constitute up to 80% by volume so stably held in the cells that the extractable perfume oil is not substantially in excess of 5% in accordance with U.S. Pat. No. 3,971,852 issued on July 27, 1976 and incorporated herein by reference;
c. Emulsion polymerization forming capsules around microdroplets of fragrance oil according to the teachings of U.S. Pat. Nos. 3,423,489 and 3,516,941, the disclosures for which are incorporated by reference herein;
d. Encapsulation by means of coacervation as disclosed in U.S. Pat. Nos. 2,800,457; 2,800,458; 3,041,289 and 3,533,958 the disclosures for each of which is incorporated by reference herein.

3. Substantially uniformly distributing the resulting second suspension in a consumable liquid such as ethanol or an ethanol-water solution to form a hydro-alcohol composition of matter (e.g., cologne) or marketing the resultant solid or gel material "as-is".

In summary, in carrying out the process of our invention, sustained release fragrances are prepared by combining non-confined fragrance oils with encapsulated or physically entrapped fragrance oils. These combinations are fashioned so that the free fragrance oil or fragrance oil emulsion are bound in a network of physically entrapped fragrance oil and suspending agent. The thixatropic pastes or free-flowing powders which result are products where the unconfined fragrance oil or unconfined fragrance oil emulsion, the "encapsulated" or physically entrapped fragrance oil and suspending agent are held together by physical forces.

Although the fragranced materials and hydro-alcohol compositions of matter (e.g., colognes, after-bath splashes and after-shave lotions) of our invention can be prepared from single fragrance oils, e.g., patchouli oils or vetiver oils or rose oils or synthetic vetiver oil compositions or synthetic rose oil compositions, it is possible to extend the range of properties of the organoleptically utilizable composition, e.g., cologne, by use of combinations of two or more physically entrapped fragrance compositions (physically entrapped in one or more manners, e.g., spray-dried gums and encapsulation as by coacervation) and/or two or more non-confined fragrances or fragrance emulsions which may or may not be different but which are organoleptically compatible with the physically entrapped fragrances. For example, it is possible to separately prepare spray-dried fragrance compositions from gelatins of various Blooms and then to add these compositions to the first suspension of fragrance oil or fragrance oil emulsion and suspension agent (e.g., hydroxypropyl cellulose) and also add spray-dried fragrance alone to ethanol and water mixtures to form an individual hydro-alcohol composition of matter (e.g., cologne or after-shave lotion). Thus, such a hydro-alcohol composition of matter (e.g., cologne) may, for example, contain a mixture of fragrance compositions prepared from a low Bloom gelatin (characterized by a rapid fragrance release) and a high Bloom gelatin (characterized by a longer fragrance release on use thereof and in contact with the skin) as well as non-confined fragrance oil or fragrance oil emulsion (very rapid release). The properties of these resultant colognes will be intermediate to the properties obtained from each of the fragrance compositions when used separately. Specifically, if a fragrance composition formed from 50 Bloom gelatin is mixed with a fragrance composition formed from 200 Bloom gelatin and the mixture is both (i) added to a fragrance oil and suspension agent which composition is added to, for example, a cologne and (ii) added to the hydro-alcohol composition of matter (e.g., the cologne) alone, the product may have a fragrance release which is substantially more even over the use period than is the case when single fragrance compositions just containing the entrapped and non-confined fragrance oils or emulsions and suspension are employed.

Similarly, it is possible to modify the properties of the perfume compositions of our invention by use of mixtures of physically entrapped fragrance compositions, e.g., spray-dried fragrance compositions characterized by different ratios of entrapment agent to fragrance oil. If, for example, a composition containing 10% fragrance agent and 90% gelatin is mixed with one containing 50% fragrance agent and 50% gelatin, the resulting blended fragrance composition after adding non-confined fragrance oil or fragrance oil emulsion and suspension agent, will yield a composition having a more even (in relation to duration of use activity time) liberation of fragrance than is obtained by use of either fragrance agent alone.

Liberation of fragrance from the perfume compositions of our invention may also be modified in a controlled manner to obtain a even, sustained fragrance level from the time that use begins and thereafter for a protracted period of time far in excess of that obtained today in such colognes by using various mixtures of fragrance compositions (a) having different particle size of physically entrapped fragrance, the resulting product deriving much of its initial fragrance from the smaller particles and much of its later fragrance from the larger particles or (b) formed from gelatins of different pH (the composition formed from gelatin of higher pH (e.g. 6) giving quick release of fragrance while that formed from lower pH (e.g. 2.5) giving slower release).

A particularly desirable fragrance composition of our invention contains unfixed fragrance, spray-dried fragrance and suspension agent, hydroxypropyl cellulose, in proportions of about 1:1:0.1. This product is characterized by an interesting or pleasing fragrance level which may start at 0.25 seconds from the point of contacting the cologne with the skin on use thereof. Over substantially the entire period of fragrance release, the fragrance level is higher than that of the standard fragranced cologne and the fragrance is continuous, rich, full and true.

Thus, in summary, the term "encapsulate" may be used to describe the relation of the entrapment agent and the fragrance agent and may mean either (a) that the latter in the form of spray-dried emulsions of discrete microdroplets is distributed substantially uniformly within or in the interstices of finely divided particles of the former or (b) that the fragrance agent is locked within polymerized capsule walls where the polymer is a urea formaldehyde polymer or the like. Thus, for example, the fragrance agent is locked within the entrapment agent (e.g., gelatin, gum acacia, urea formaldehyde resin, dextrin, modified food starch, suspension polymerizate, wax, hydroxypropyl cellulose, or emulsion polymerizate) to the extent that the former is released substantially only as the molecules of entrapment agent are either (a) dissolved from the individual entrapment agent particles by the hydrolytic action of, for example, sweat glands or (b) eliminated from the individual entrapping particles as a result of the application of positive mechanical pressure created, for example, by rubbing or washing or the normal abrading of articles of clothing against the skin on wearing of said articles of clothing.

The following examples illustrate processes for preparing individual fragrance compositions necessary to produce the fragrance compositions useful in our invention.

EXAMPLE A

The following fragrance formula is provided:

| Ingredient | Parts by Weight |
| --- | --- |
| Phenylethyl alcohol | 175 |
| Geraniol | 400 |
| Trichloromethylphenyl carbinyl acetate | 20 |
| Phenylethyl acetate | 60 |
| Undecylenic aldehyde (10% in | 5 |

-continued

| Ingredient | Parts by Weight |
| --- | --- |
| diethyl phthalate) | |
| n-nonyl aldehyde (10% in diethyl phthalate) | 2 |
| Musk ketone | 10 |
| Musk ambrette | 10 |
| Eugenol phenyl acetate | 20 |
| Citronellol | 100 |
| Vanillin (10% in diethyl phthalate) | 6 |
| Eugenol | 30 |
| Citronellyl formate | 30 |
| Geranyl acetate | 10 |
| Linalool | 40 |
| Geranyl phenyl acetate | 50 |
| Cis beta, gamma-hexenyl acetate | 2 |
| Bicyclo[2,2,2]octenemethanol serivative mixture having the formula: prepared according to Example III of U.S. Pat. No. 4,163,737 the disclosure for which is incorporated by reference herein | 25 |
| | 100 total |

The instant rose formulation has an intense rose aroma with great floralcy and woodyness with clary-sage and violet leaf nuances.

EXAMPLE B 20 grams of the fragrance composition of Example A is emulsified in a solution containing 300 grams gum acacia and 700 grams water. The emulsion is spray-dried with a Bowen Lab Model Drier utilizing 250 c.f.m. of air with an inlet temperature of 500° F., an outlet temperature of 200° F. and a wheel speed of 50,000 r.p.m.

EXAMPLE C 130 grams of vetiver oil redistilled is emulsified in a solution containing 300 grams of "Nadex" dextrin (manufactured by National Starch and Chemical Co. of New York, N.Y.) and 700 grams of water. The emulsion is spray-dried with a Bowen Lab Model Drier utilizing 250 c.f.m. of air with an inlet temperature of 500° F., an outlet temperature of 200° F., and a wheel speed of 50,000 r.p.m.

EXAMPLE D 10 parts by weight of 50 Bloom pigskin gelatin is added to 90 parts by weight of water at a temperature of 150° F. The mixture is agitated until the gelatin completely dissolves and the solution is cooled to 120° F. 20 parts by weight of the perfume composition of Example A is added to the solution which is then homogenized to form an emulsion having a particle size typically in the range of 2–5 microns. This material is kept at 120° F. under which conditions the gelatin will not jell.

Coacervation is induced by adding, slowly and uniformly, 40 parts by weight of a 20% aqueous solution of sodium sulfate. During coacervation, the gelatin molecules are deposited uniformly about each oil droplet as a nucleus.

Gelation is effected by pouring the heated coacervate mixture into 1,000 parts by weight of 7% aqueous solution of sodium sulfate at 65° F. The resulting jelled coacervate is then filtered and washed with water at a temperature below the melting point of gelatin to remove the salt.

Hardening of the filtered cake is effected by washing with 200 parts by weight of 37% solution of formldehyde in water. The cake is then washed to remove residual formaldehyde.

EXAMPLE E

A 40% dextrin solution is freeze-dried. This is accomplished by a conventional technique such as that described in column 4 of U.S. Pat. No. 3,404,007.

The freeze-dried material is then milled to a particle size of 20–40 mesh.

100 grams of this freeze-dried material are then combined with 50 grams of patchouli oil redistilled (East Indies). This is accomplished by mixing the materials in a suitable blender such as a ribbon blender. This results in a dry, free-flowing powder having the advantages heretobefore described. To ensure against atmospheric reaction or vaporization of the patchouli oil in the solid matrix, the powder is given a protective coating to seal the entrances to the interstices or cavities in the porous particulate matrix. One suitable form of coating is a dextrin solution which has the property of forming an impermeable film for preventing the escape or permeation of the fragrance oil.

EXAMPLE F 2-hydroxyethyl methacrylate (100 parts) is stirred with 0.05 parts by weight t-butyl peroctoate in a nitrogen atmosphere at a temperature of 40° C. for 30 minutes. The resultant mixture is cooled to 25° C. and a further 0.10 parts by weight of t-butyl peroctoate is added, ethylene glycol dimethacrylate (0.1 part) being added at the same time. To this casting solution, oil of galbanum natural is added in an amount of 10 parts by weight. After curing and granulation, the fragranced powder is used as part of a fragrance releasing formulation as exemplified infra.

EXAMPLE G

A. Preparation of Capsule Composition 500 grams of water are heated to boil and 500 grams of dextrin (National Starch and Chemical Corporation, 78-1523) is added with rapid and efficient mixing using a closed turbine, high shear mixer (Barrington CONVERTI JET Model CJ-5B). Mixing is continued until a homogeneous solution is obtained.

B. Preparation of Petitgrain Oil Capsule Composition 81 grams of petitgrain oil Paraguay is emulsified in 300 grams of the shell composition solution (A) by means of a homogenizing mixer (Barrington CONVERTI JET Model CJ-5B operated as a closed turbine unit). At the start of the operation, the temperature of the matrix composition solution is 20° C. and of the petitgrain oil is 15° C. The mixing vessel is cooled during the operation of the mixing in order to prevent a rise in temperature and to keep the temperature below 20° C.

C. Capsule Formation and Dehydration 1000 grams of polyethylene glycol having an average molecular weight of 400 (Union Carbide Corporation, Carbowax 400) and at a temperature of about 25° C. is placed in a vessel equipped with homogenizing mixer (Barrington CONVERTI JET Model CJ-5B operated as an open turbine unit). 100 grams of the petitgrain oil capsule composition (B) is introduced into the polyethylene glycol in a thin stream with steady medium speed operation of the mixer (about 1,500 rpm shaft speed). By the action of the mixer, the petitgrain oil emulsion is broken up into coarse liquid particles, which in contact with the polyethylene glycol, are rapidly converted into gel particles and finally into virtually anhydrous granules.

The capsule granules are separated from the excess polyethylene glycol by means of a basket centrifuge and used in "cologne" suspensions as set forth in the examples, infra.

EXAMPLE H

According to the process of U.S. Pat. No. 3,971,852, Example 1 at column 12, a solution of encapsulant comprising 32 parts of glucoronolactone and 48 parts of the polysaccharide having the following units:

sorbitol
erythritol
fructose
sucrose
D-glucoronolactone
glucose
glycerine
maltose
mannitan
methyl-A-D-glycopyranoside
raffinose
ribitol
sorbitan is prepared by dissolving them in 250 parts of water with agitation at high speed in a household type Waring blender. Sandalwood oil (EI) is slowly added to the resulting solution until 120 parts are incorporated while continuing high speed agitation for 3 minutes at which time an oil/water emulsion has formed with an average droplet diameter of 0.5 microns. The viscosity is determined with a Brookfield Model LVT Viscosimeter is 57.5 centpoises at 30° C. The proportions are chosen to give a sandalwood oil loading of 60% (120 parts sandalwood oil and 80 parts encapsulant). The resulting mixture is spray-dried in a standard Anhydro laboratory drier, size No. 1, maintained at an air inlet temperature of 180° C. and an air outlet temperature of 90° C. at a feed rate of 3 pounds per hour of emulsion. There is collected 170 parts by weight of powdered product readily passing through a 140 mesh screen which, upon analysis by standard steam distillation technique, is shown to contain 56% by volume (V/W) or 56% by weight (W/W) of volatile oil based on the weight of the product. This represents an 85% weight recovery of product containing 93% of the theoretical load of sandalwood oil initially employed to make the emulsion. This represents a total recovery of 79% of the original oil. The extractable oil of the product is 0.2% as determined by extraction. The moisture content is 2.1% as determined by Karl Fisher procedure. In general the volatile oil content is determined by the standard steam distillation technique on product as produced. The volatile oil content as so determined includes the extractable oil.

EXAMPLE J

Apparatus as illustrated in FIG. 1 of U.S. Pat. No. 3,423,489 issued on Jan. 1, 1969, the disclosure of which is incorporated herein by reference, is used to form capsules of an aqueous film material in wax shells. The nozzle is inclined at an angle of 30° from the vertical. The nozzle was provided with an orifice of 0.167 mm in diameter and was immersed in the bath to a length of 1 mm. The fill liquid had the following composition:

|  | Parts |
|---|---|
| Water | 97.6 |
| Copolymer of methyl vinyl ether and maleic anhydride (commercially available under the designation "Gantrez AN-169") | 1.0 |
| Hydroxyl terminated block copolymer of ethylene oxide and propylene oxide nonionic surfactant (commercially available under the designation "Pluronic L-64") | 1.0 |
| Guiacwood oil | 0.4 |
| The shell composition was as follows: | |
| Paraffin wax, M.P. 55° C. | 44.95 |
| Parrafin wax, M.P. 83° C. | 44.95 |
| Copolymer of ethylene and ethyl acrylate (commercially available under the designation "Dow EA-2018") | 10 |
| Butylated hydroxytoluene (antioxidant) | 0.1 |

One liter of filtered fill solution was placed in the reservoir to which 1 atmosphere gauge pressure was applied. The temperature of the fill liquid was 24° C. The wax temperature was 170° C. and the tip winding was heated to about 400° C. The needle valve was opened and the fill solution was discharged at a rate of 4.5 meters per second. The Reynolds number characterizing the flow of fill liquid through the nozzle was 150 (measured before immersion in wax). The wax solidified at a distance approximately 80 cm from the orifice which was 0.4 seconds travel time of the wax in the trajectory path. The time was sufficient to permit the biliquid column formed by the discharging aqueous solution and the molten wax pulled along therewith to first form a string of capsules and then to separate into individual discrete capsules. Capsules were produced at a rate of about 60,000 per minute. The total trajectory length was about 12 feet (about 1 second total time in trajectory) after which the capsules were allowed to fall onto an inclined plane from which they proceeded to a collecting trough. The capsules collected were 700 microns in average diameter and had a shell thickness of about 50 microns. The fill liquid comprised about 63% of the total capsule volume and the shell material about 37%. The capsules are useful in preparing the colognes as set forth in the Examples I-X, infra.

The following examples are given to illustrate embodiments of our invention as it is presently preferred to practice it. It will be understood that these examples are illustrative and the invention is not to be considered as restricted thereto except as indicated in the appended claims. These examples also encompass detailed description of the drawings.

EXAMPLE I

The following mixture is prepared:

| A. Perfume composition of Example A | 2.00 parts |
|---|---|
| Food grade ethanol 95% | 19.80 parts |
| Methyl paraben (p-hydroxymethyl | 0.20 parts |

-continued

| | |
|---|---|
| benzoate) | |
| Crodesta ® F-110 (a fatty acid sucrose ester having the formula: 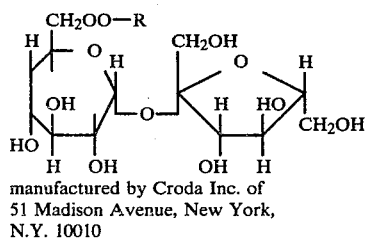 manufactured by Croda Inc. of 51 Madison Avenue, New York, N.Y. 10010 | 1.00 parts |

This mixture is mixed at room temperature using a propellant-type mixer until the mixture is uniform. The following mixture is prepared:

| | | |
|---|---|---|
| B. | Ben-A-Gel ® EW (a specially processed smectite clay gellant having a specific gravity of 2.5; a density of 20.9 pounds per gallon and a bulking value of 0.0479 gallons per pound manufactured by N L Industries of Hightstown, N.J.) | 0.48 parts |
| | Distilled water | 72.52 parts |

The resulting mixture is mixed using a propellant type mixer until a smooth gel is formed.

The smooth gel (B) is added to mixture (A) slowly, using a propeller-type mixer.

Microencapsulated perfume prepared according to Example J (4.00 parts) are added to the resultant mixture of B and A using a propellant type mixer until the capsules are uniformly dispersed.

Part of the resulting material is marketed as is as a "rose/guiacwood" dry cologne. The other portion is marketed in admixture with 80%, 85%, 90% and 95% food grade ethanol at the levels of 2%, 2.5%, 3%, 5%, 10% and 15% of "solid cologne mixture".

On use, the resulting cologne displays, initially, an intense rose fragrance. After 5 hours, the resultant cologne displays an interesting guiacwood fragrance. The wearer of the cologne retains a pleasant guiacwood fragrance for 24 hours thereafter. In addition, the resulting cologne has the effect of covering any undesirable aromas on the wearer or associated with the wearer.

FIG. 1 is a photomicrograph of the suspension produced according to the instant example prior to admixture with ethanol. (200X magnification)

Figure 3:
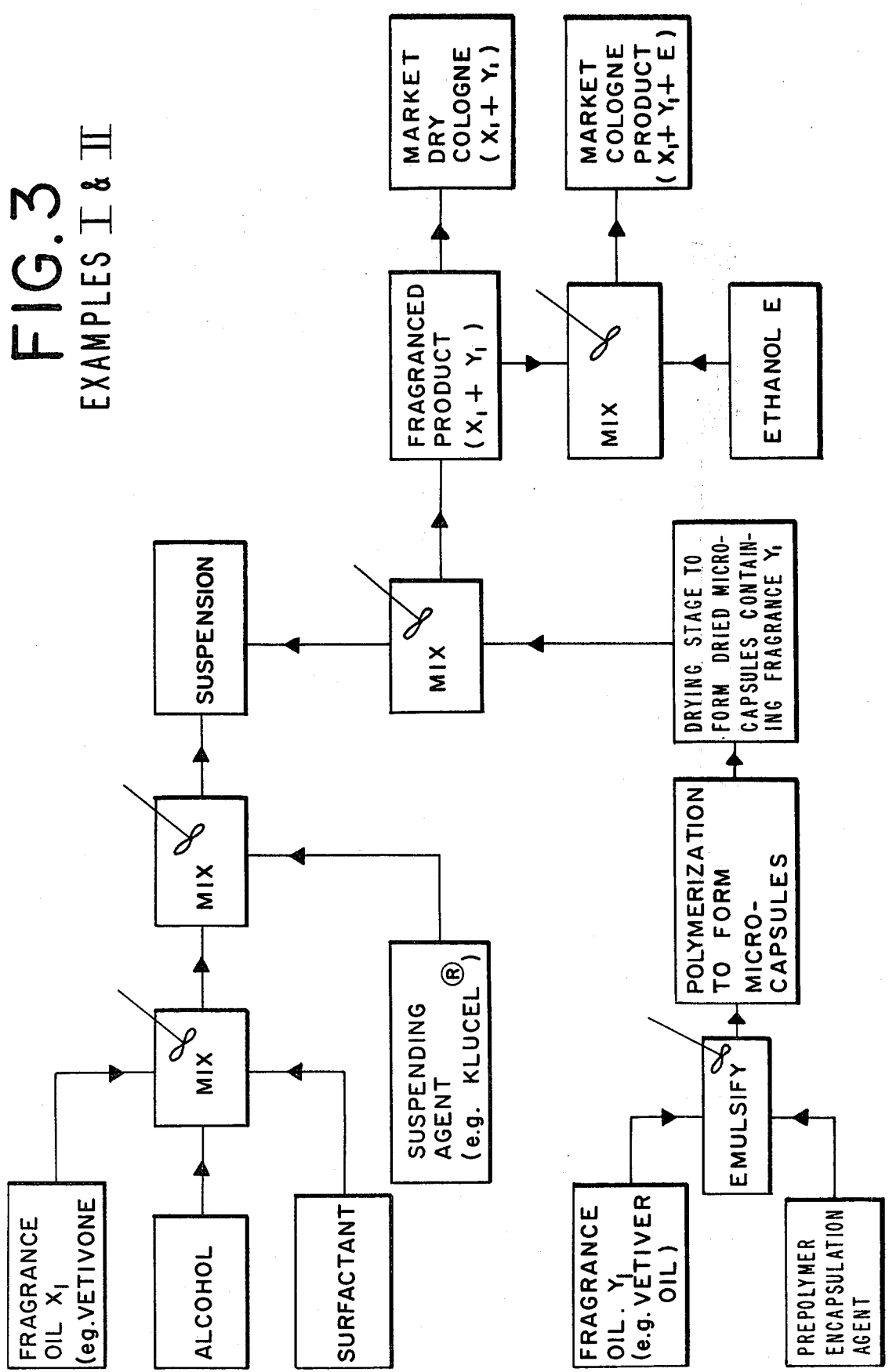
FIG. 3 sets forth a block diagram flow sheet indicating the preparation of a fragranced cologne powder and fragranced cologne liquid of our invention as more fully described in Examples I and II.

FIG. 3 is a block diagram-flow sheet of the above-described process.

Using a Brookfield Model LV Viscosimeter, the following viscosity readings are made:

(Spindle No. 1)
12 rpm = 200 centipoises
30 rpm = 114 centipoises
60 rpm = 76 centipoises An experiment similar to that of the immediately preceding example is carried out except that the pH of the resultant suspension is adjusted to 5.5 using phosphoric acid.

The resultant viscosity using a Brookfield Model LV Viscosimeter, Spindle No. 1, is as follows:

6 rpm = 595 centipoises
12 rpm = 377.5 centipoises

An experiment similar to that carried out above is carried out except that instead of 2 parts by weight of fragrance in mixture "A", 4 parts by weight of fragrance is used and instead of 72.52 parts by weight of Ben-a-Gel ®EW, 67.0 parts is used and instead of 4.0 parts by weight of capsules prepared according to Example J, 8.0 parts by weight of capsules prepared according to Example J is used.

The resultant viscosity using a Brookfield Model LV Viscosimeter, Spindle No. 1, is as follows:

6 rpm = 555 centipoises
12 rpm = 355 centipoises

An experiment similar to the immediately preceding example is carried out except that the Ben-A-Gel® concentration is at 1.7 times that used in the immediately preceding concentration (1% Ben-A-Gel® in water). The resulting viscosity is as follows:

Using a Brookfield Model LV Viscosimeter, Spindle No. 2:

6 rpm = 1,100 centipoises
12 rpm = 650 centipoises
30 rpm = 350 centipoises

The results of each of these additional experiments are identical to those set forth above.

EXAMPLE II

The following mixture is prepared:

| | | |
|---|---|---|
| A. | Fragrance prepared according to Example A | 2.00 parts |
| | Ethyl alcohol (food grade 95% aqueous) | 19.80 parts |
| | Methyl paraben | 0.20 parts |
| | Crodesta ® F-110 | 1.00 parts |

The resulting mixture is mixed at room temperature using a propellant type mixer until the mixture is uniform.

The following mixture is then prepared:

| | | |
|---|---|---|
| B. | SGP ® polymer 502-S manufactured by the Henkel Corporation of 4620 W. 77th Street, Minneapolis, Minnesota 55435, a starch based absorbent polymer produced according to the following U.S. Pat. Nos.: 3,935,099 3,981,100 3,985,616 3,997,484 the disclosures of which are incorporated by reference herein | 0.29 parts |
| | Distilled water | 73.71 parts |

This mixture is mixed using a propellant type mixer until a clear gel is formed.

Mixture B is added to mixture A slowly using a propellant type mixer.

Microcapsules prepared according to Example J (4.00 parts) are added to the mixture of B and A using a propellant type mixer until the capsules are uniformly dispersed.

The viscosity of the resultant suspension using a Brookfield model LVI Viscosimeter (spindle No. 3) is as follows:

6 rpm: 6700 centipoises
12 rpm: 4300 centipoises 30 rpm: 2460 centipoises

Figure 2:
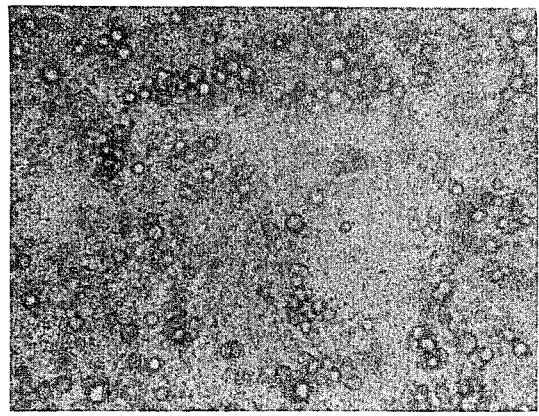
FIG. 2 is a photomicrograph of the cologne suspension produced according to Example II (200X magnification).

FIG. 2 is a photomicrograph of the resulting suspension (200X magnification).

The resulting material may be marketed as a "dry cologne" or may be admixed with ethanol as follows:
2% suspension;
4% suspension;
8% suspension;
12% suspension;
20% suspension;
in 80%, 85%, 90% and 95% food grade ethanol.

When the suspensions are used, the user experiences the evolvement, initially, of a high intensity rose aroma which lasts for 50 hours. This is followed by a pleasant lower intensity guiacwood aroma which lasts for 30 hours. In addition, there is an unexpected and surprising effect of deodorancy attached to the use of this cologne which lasts for 36 hours.

FIG. 3 sets forth a block diagram-flow sheet for the process of this example.

EXAMPLE III

The following mixture is prepared:

| Ingredients | Parts by Weight |
|---|---|
| Liquid fragrance composition of Example A | 48.4 |
| KLUCEL ® type EF (brand of hydroxypropyl cellulose manufactured by Hercules Corporation of Wilmington, Delaware having a molecular weight of about 50,000 and having a viscosity defined according to FIG. 12) | 3.2 |

The KLUCEL ®EF is dispersed in the viscous liquid flavor composition of Example A with vigorous stirring, thereby resulting in a viscous liquid. 48.4 parts by weight of the powder fragrance composition of Example B is then blended into such viscous liquid with stirring at 25° C. for a period of 30 minutes resulting in a thixotropic sustained release fragrance paste.

The resulting fragrance paste has a rose aroma initially on admixing with 2%, 4%, 6%, 8%, 10%, 12% and 20% in 80%, 90%, and 95% aqueous food grade ethanol. The wearer continues to evolve the pleasant rose fragrance over a period of 24 hours at closely similar intensity levels.

Figure 4:
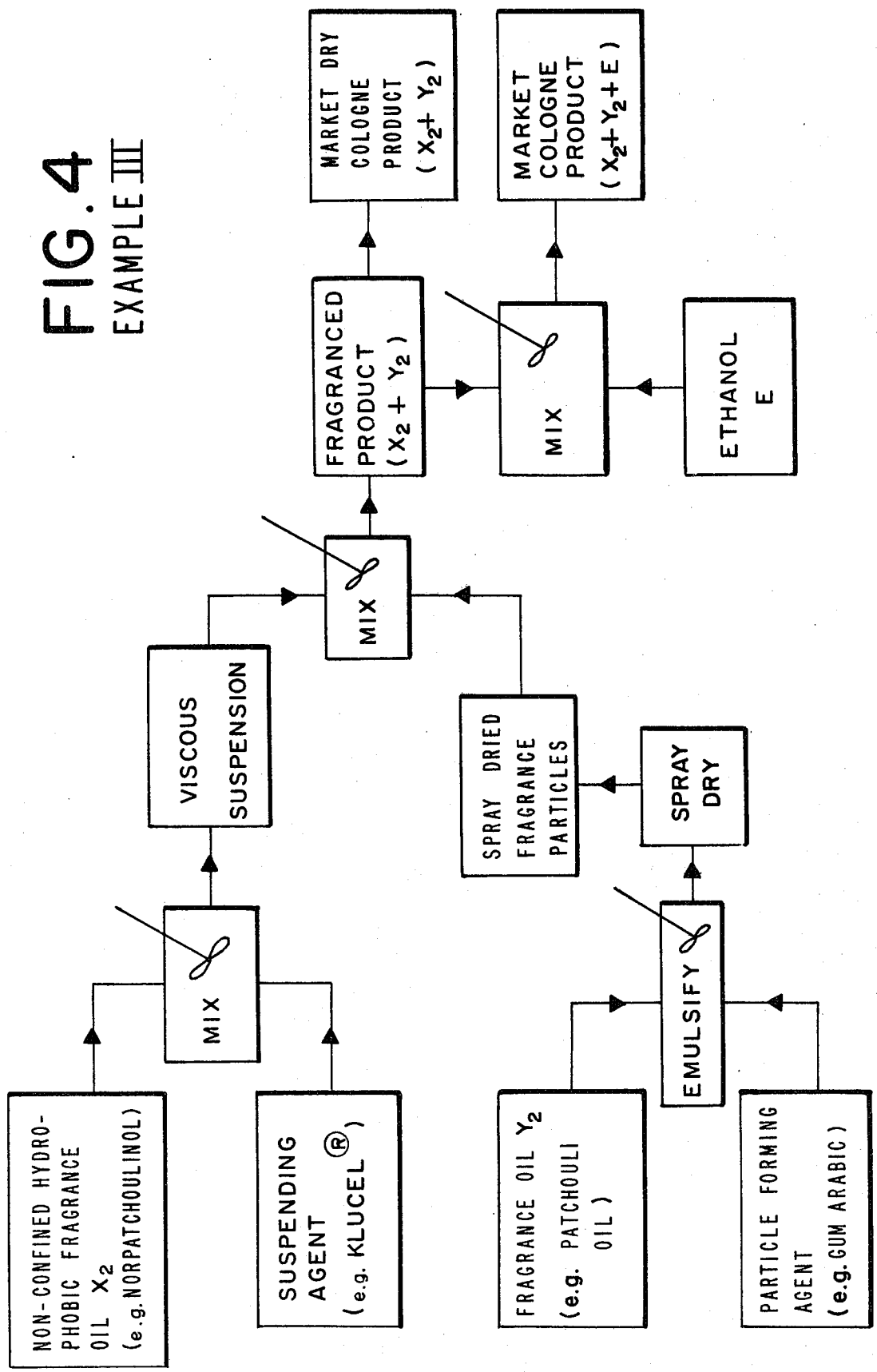
FIG. 4 sets forth a block diagram flow sheet indicating the preparation of the fragranced cologne powder and fragranced cologne liquid of our invention as more fully described in Example III.

FIG. 4 is a block flow diagram of the process of this example.

EXAMPLE IV

The following mixture is prepared:

| Ingredients | Parts by Weight |
|---|---|
| Natural patchouli oil | 26 |
| KLUCEL ® LF (manufactured by the Hercules Corporation of Wilmington, Delaware having a molecular weight of about 100,000 and a viscosity defined according to FIG. 12) | 9 |

The KLUCEL ®LF is dispersed in the patchouli oil with vigorous stirring thereby resulting in a viscous liquid. 65 parts by weight of the the powder fragrance composition of Example D is then blended into the viscous liquid with stirring at 25° C. for a period of 30 minutes resulting in a dry, free-flowing sustained release fragrance powder called a "dry cologne product" and either marketed as such or admixed at levels of 2%, 4%, 6%, 8%, 10%, 12%, 20% and 25% in 80%, 90% and 95% aqueous food grade ethanol.

On use of the resulting colognes, the wearer evolves a pleasant patchouli fragrance initially followed by, after 5 hours, a pleasant rose fragrance for a period of 30 hours thereafter.

Figure 5:
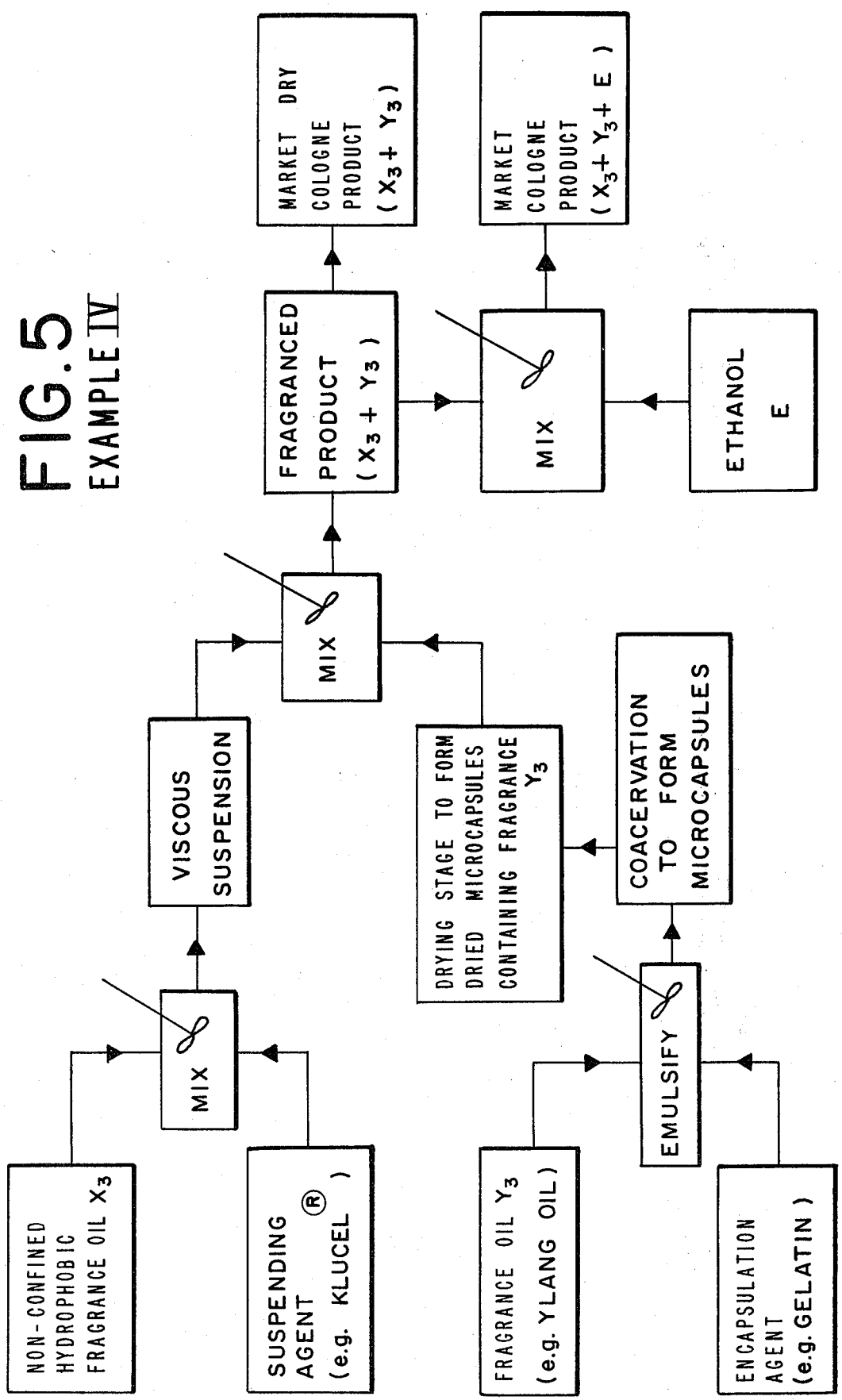
FIG. 5 sets forth a block diagram flow sheet indicating the preparation of the fragranced cologne powder as well as the fragranced cologne liquid of our invention as more fully described in Example IV.

FIG. 5 sets forth a block diagram-flow sheet of the process of this example.

EXAMPLE V

The following mixture is prepared:

| Ingredients | Parts by Weight |
|---|---|
| Patchouli oil | 47.25 |
| Propylene glycol | 0.50 |
| KLUCEL ® JF (brand of hydroxypropyl cellulose manufactured by the Hercules Corporation of Wilmington, Delaware having a molecular weight of about 120,000 and a viscosity defined according to FIG. 12) | 5.00 |

The KLUCEL ®JF is dispersed in the patchouli oil with vigorous stirring thereby resulting in a viscous liquid. 47.25 parts by weight of the powder fragrance composition of Example E is then blended into said viscous liquid with stirring at 25° C. for a period of 30 minutes resulting in a thixotropic sustained release fragrance paste.

47.25 parts by weight of the powder fragrance composition of Example H (sandalwood fragrance) is then blended into said thixotropic sustained release fragrance paste with stirring at 25° C. for a period of 60 minutes resulting in a sustained release fragrance powder. The sustained release powder is marketed per se or admixed at the rates of 2%, 4%, 6%, 8%, 10%, 12%, 16%, 20% and 30% in 80%, 85%, 90% and 95% food grade ethanol thereby yielding a group of cologne liquids.

Figure 7:
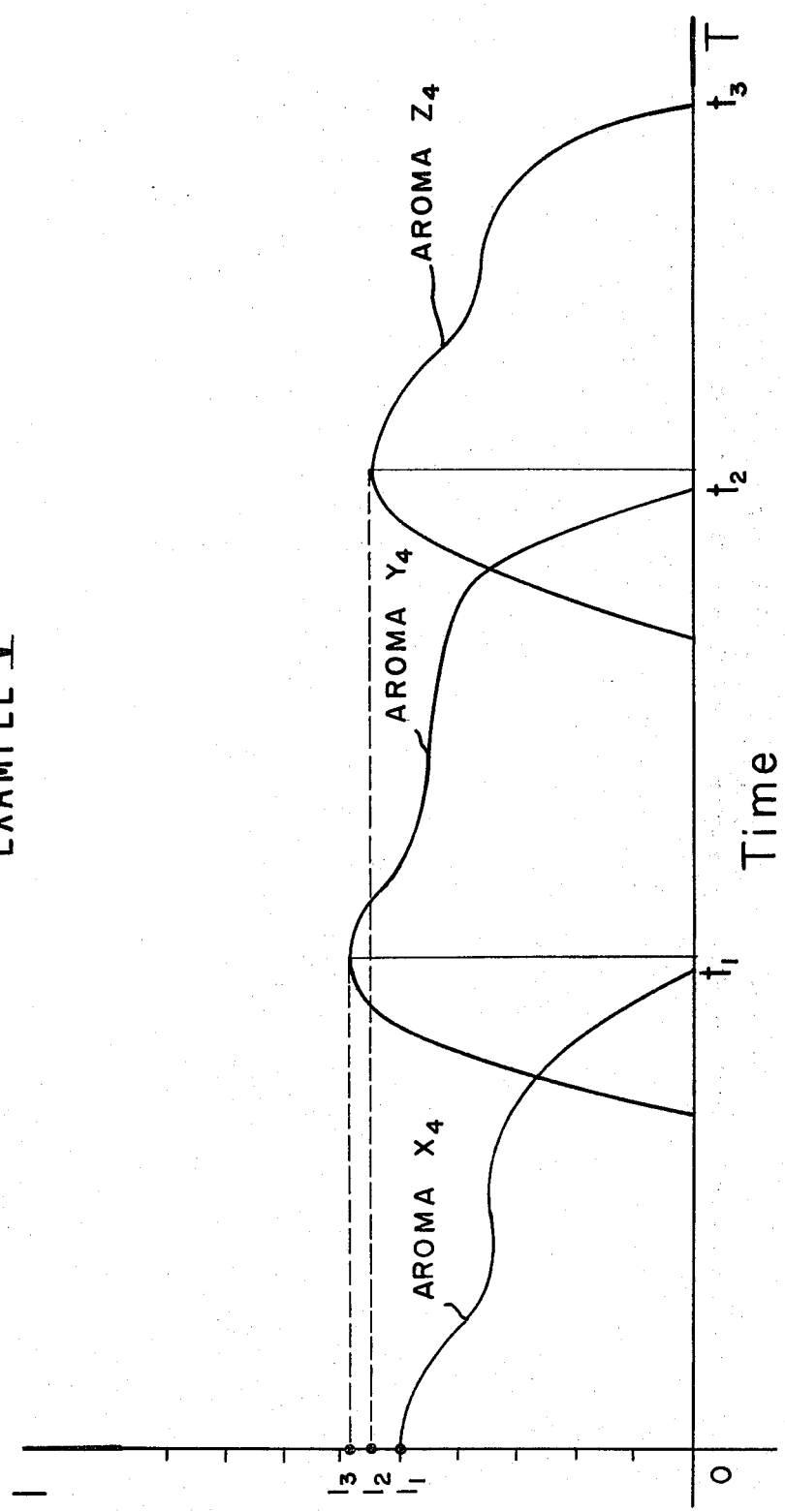
FIG. 7 sets forth a graph of intensity of perceptible, desirable aroma evolved from the subject vs. time for each of the individual aromas evolved as a result of the use of the fragranced cologne and the fragranced cologne liquid prepared according to Example V.

On use, each of the cologne liquids yield for times set forth in FIG. 7, first patchouli fragrances; then for a brief period of time, a patchouli/sandalwood fragrance and finally, for a period of 30 hours, a sandalwood fragrance. The patchouli fragrance itself, lasts for a period of about 8 hous. The actual intensity vs. time graph for aromas $X_4$ and $Y_4$ are indicative of patchouli aromas and the graph for fragrance $Z_4$ is indicative of sandalwood aroma.

Figure 6:
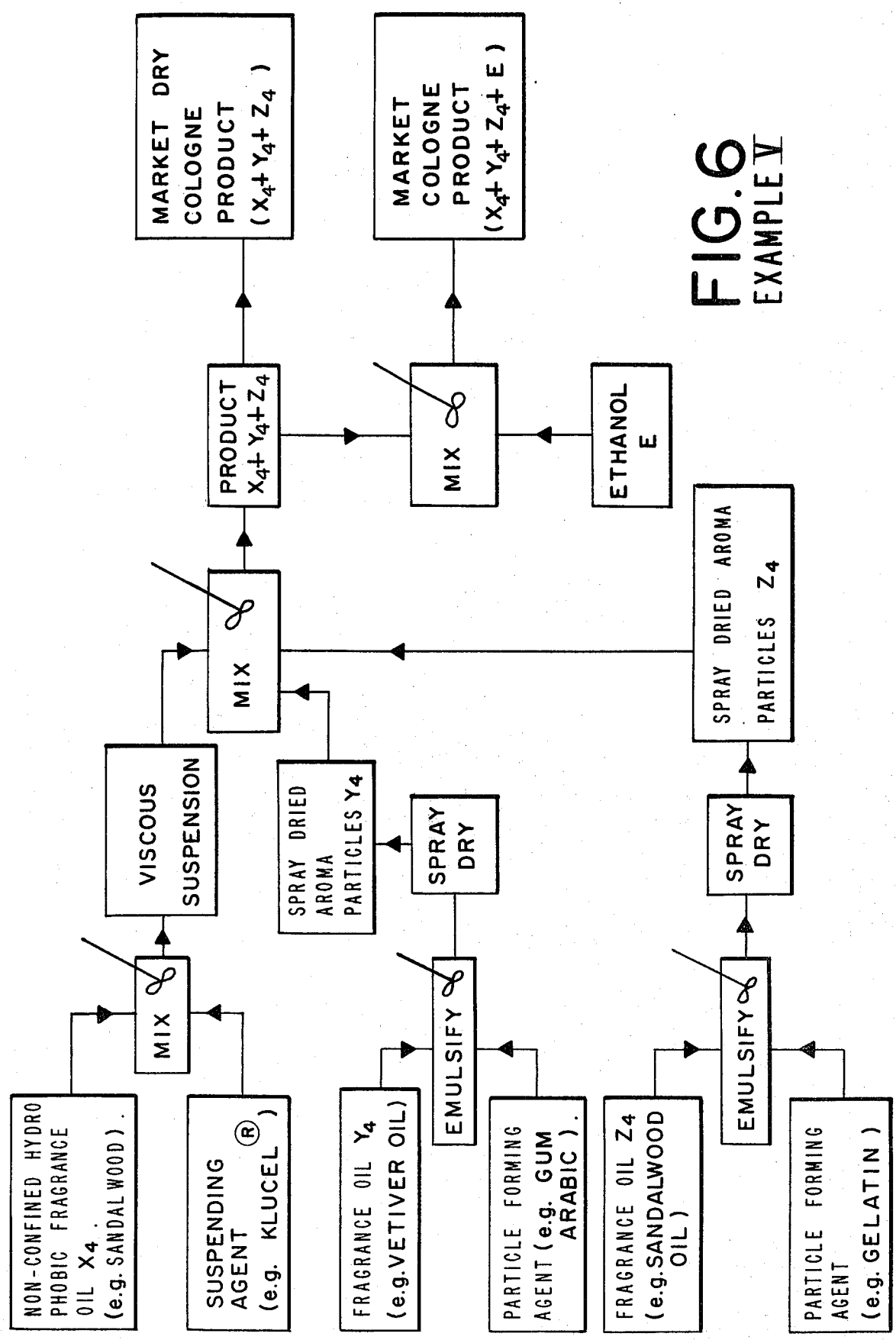
FIG. 6 sets forth a block diagram flow sheet indicating the preparation of another embodiment of our invention which is a fragranced cologne powder and a fragranced cologne liquid which evolves on use at controlled periods of time different fragrances as more fully described in Example V.

FIG. 6 sets forth the flow sheet-block diagram for the process of this example.

EXAMPLE VI

The following mixture is prepared:

| A. Ylang oil | 2.0 parts by weight |
|---|---|
| Ethyl alcohol (95% food grade) | 19.8 parts by weight |
| Methyl paraben | 0.2 parts by weight |
| Crodesta ® F-110 | 1.50 parts by weight |

This mixture is mixed at room temperature using a propellant type mixer until the mixture is uniform.

The following mixture is then prepared:

| B. | Ben-A-Gel ® EW | 0.85 parts by weight |
| | Distilled water | 72.52 parts by weight |

The resulting mixture is mixed in a propellant type mixer until a smooth gel is formed.

C. To the mixture of "A" and "B" is added galbanum-containing polymer prepared according to Example F. The resulting mixture is mixed in a propellant type mixer until the powder is uniformly dispersed.

The following mixture is prepared:

| D. | Galbanum oil | 2.0 parts by weight |
| | Ethyl alcohol | 19.80 parts by weight |
| | Methyl paraben | 0.20 parts by weight |
| | Crodesta ® F-110 | 1.50 parts by weight |

The resulting mixture is mixed using a propellant type mixer until the mixture is uniform.

The following mixture is prepared:

| E. | Ben-A-Gel ® EW | 0.48 parts by weight |
| | Distilled water | 72.52 parts by weight |

The resulting mixture "E" is mixed until a smooth gel is formed.

Mixture "E" is added to mixture "D" slowly using a propeller type mixer.

F. Using a propellant type mixer, the petitgrain oil capsules prepared according to Example G are added to "D" and "E" until the capsules are uniformly dispersed.

The mixtures of "A", "B", "C" and "D", "E", "F" and then intimately admixed in a propellant type mixer until a smooth blend is formed which is a solid mixture of the materials which is a solid powder. This solid powder is marketed as is as a "dry cologne" or is admixed with ethanol at the following rates: 2%, 2.5%, 3%, 4%, 5%, 10%, 20%, 25% and 30% in 75%, 80%, 85% and 90% food grade ethanol. The resulting colognes on use as a result of either (a) the hydrolytic action of body sweat or (b) the application of positive mechanical pressure to the particles which entrap the fragrances, yields fragrances first for a period of 12 hours as galbanum and then for a period of 35 hours as petitgrain.

Figure 8:
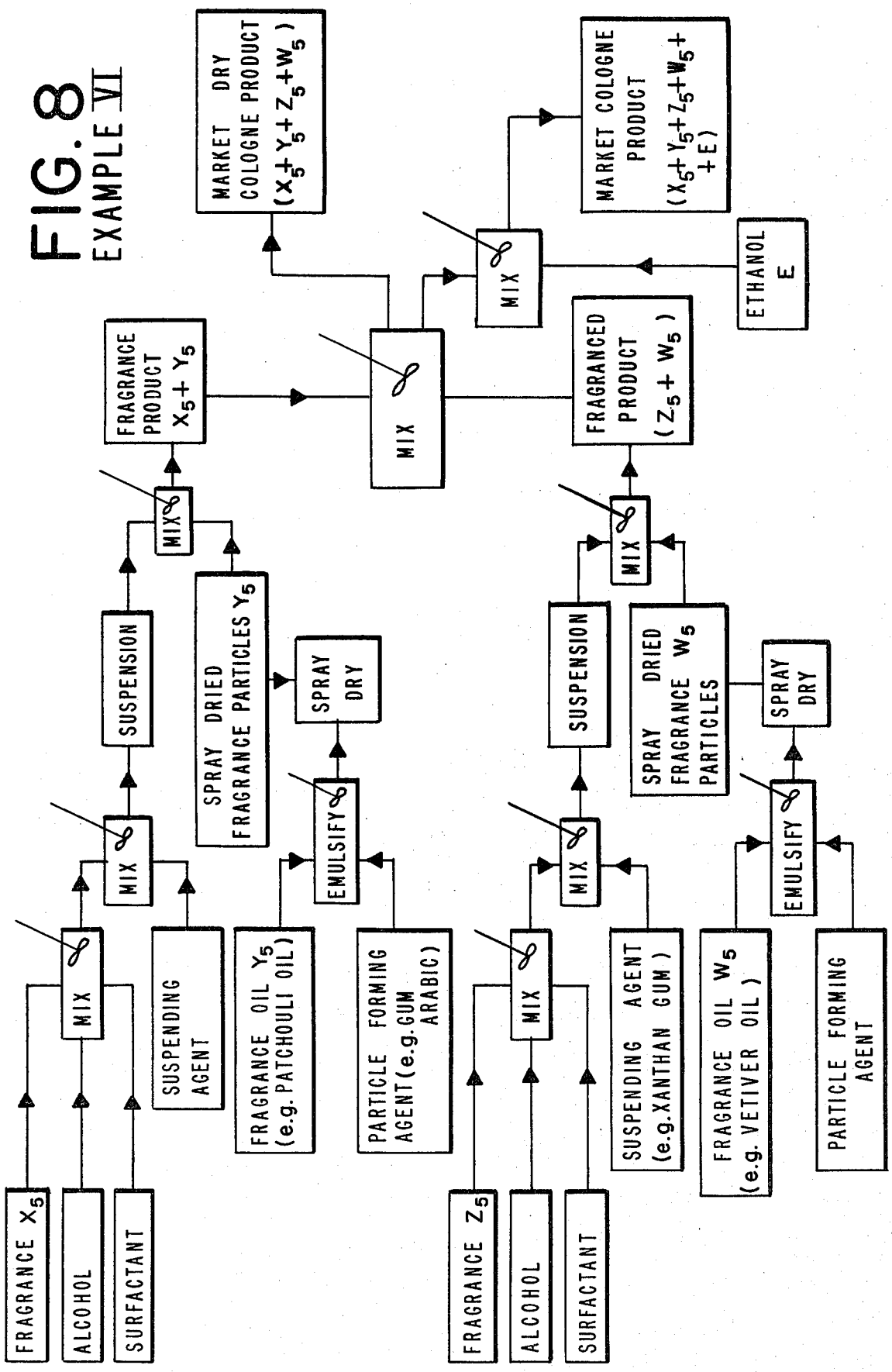
FIG. 8 sets forth a block diagram flow sheet indicating the preparation of the fragranced cologne powder as well as the fragranced cologne liquid of our invention as more fully described in Example VI wherein on use the fragranced cologne powder and the fragranced cologne liquid evolve to different fragrances over two different periods of time in a controlled manner.

FIG. 8 sets forth a block flow diagram for the process of this example.

EXAMPLE VII

The following mixture is prepared:

| A. | Sandalwood fragrance | 2.00 parts by weight |
| | Ethyl alcohol | 19.80 parts by weight |
| | Methyl paraben | 0.20 parts by weight |
| | Crodesta ® F-110 | 1.00 parts by weight |

The resulting mixture is mixed using a propellent type mixer until the mixture is uniform at 25° C.

The following mixture is prepared:

| B. | SGP ® polymer 502-S | 0.32 parts by weight |
| | Distilled water | 72.71 parts by weight |

Mixture "B" is mixed using a propellant type mixer until a clear gel is formed at 25° C.

Mixture "B" is added to mixture "A" slowly using a propellant type mixer.

C. Using a propellant type mixer, the capsuls produced according to Example C (vetiver oil) are added to the mixture of "B" and "A" until the capsules are uniformly dispersed. The resulting mixture is denominated $X_6+Y_6$. Mixture $X_6+Y_6$ is then admixed with the following mixture in a propellant type mixer at 25° C.:

The following mixture is prepared:

| Vetiver oil | 47.25 parts by weight |
| Propylene glycol | 0.50 parts by weight |
| KLUCEL ® HF (brand of hydroxypropyl cellulose produced by the Hercules Corporation of Wilmington, Delaware having a molecular weight of about 800,000 and a viscosity defined according to FIG. 12) | 5.00 parts by weight |

The KLUCEL ®HF is dispersed in the vetiver oil with vigorous stirring thereby resulting in a viscous liquid. 47.25 parts by weight of the powder fragrance composition of Example C is then blended into said viscous liquid with stirring at 25° C. for a period of 30 minutes resulting in a thixatropic sustained release fragrance paste denominated as "$Z_6+W_6$".

Figure 9:
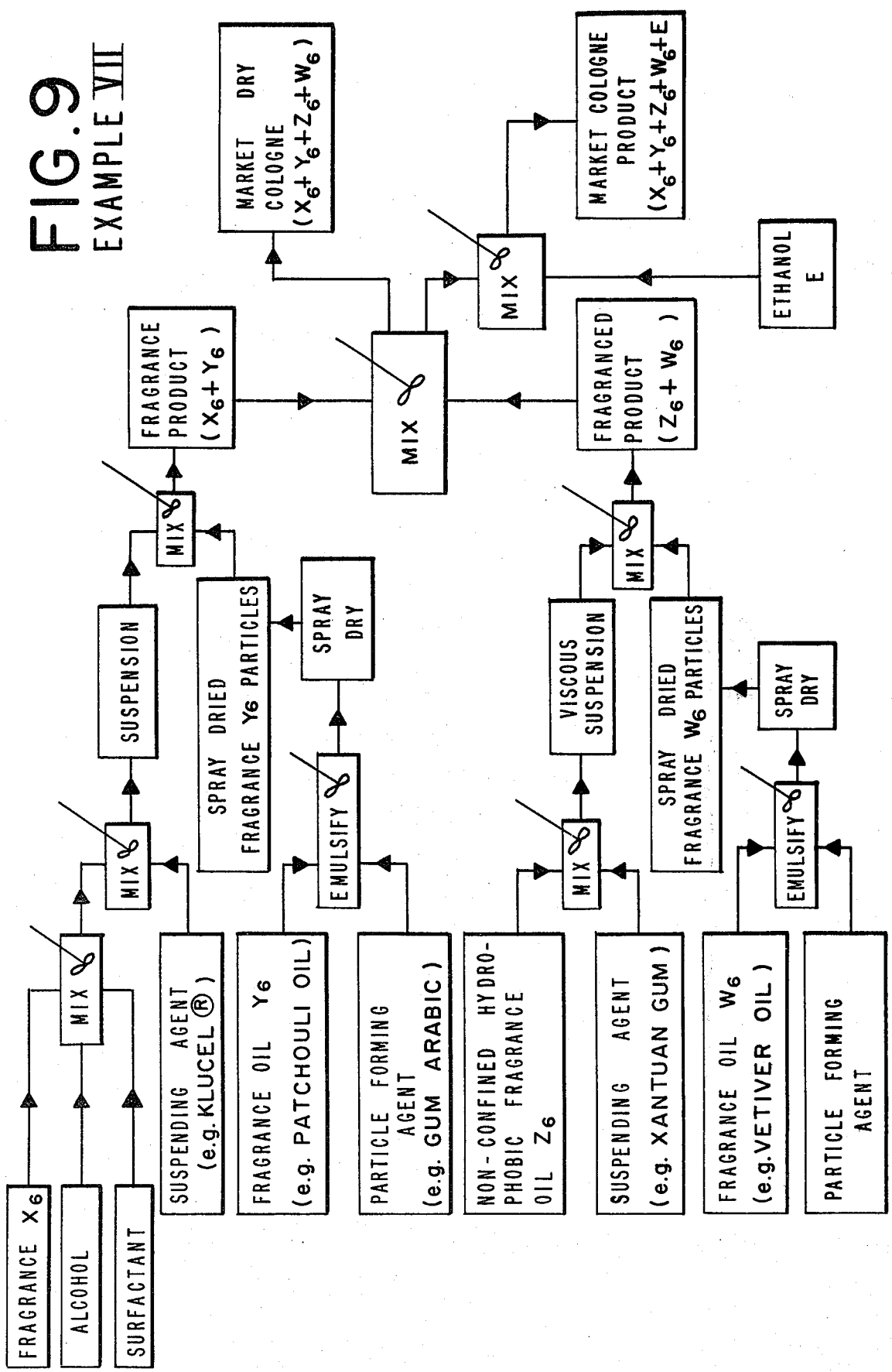
FIG. 9 sets forth a block diagram flow sheet indicating the preparation of the fragranced cologne powder as well as the fragranced cologne liquid of our invention as more fully described in Example VII wherein, on use, two different aromas are evolved at two different periods of time with high intensity and in a controlled manner.

Thus, after mixing $Z_6+W_6$ with $X_6+Y_6$, a dry cologne powder is produced denominated as $X_6+Y_6+Z_6+W_6$ in FIG. 9.

FIG. 9 is the block flow diagram for the process of this example.

The dry cologne product is either marketed or admixed with alcohol at the following rates: 2%, 3%, 5%, 10%, 15%, 30%, 35% and 40% in 75%, 80%, 85%, 90% and 95% food grade ethanol thereby yielding a cologne which on use and (a) as a result of the hydrolytic action of the sweat glands or (b) as a result of mechanical pressure applied to the particles of entrapped fragrances, yields a very long-lasting woody fragrance having sandalwood and vetiver notes for a period of 40 hours and also giving rise to a malodor deodorant effect thereby eliminating any malodors from the body for a period of 40 hours.

FIG. 9 sets forth the block flow diagram for the process of this example.

EXAMPLE VIII

The following mixture is prepared:

| A. | Guiacwood oil | 2.0 parts by weight |
| | Ethanol | 19.8 parts by weight |
| | Methyl paraben | 0.2 parts by weight |
| | Crodesta ® F-110 | 1.00 parts by weight |

The resulting mixture is mixed at room temperature using a propellant type mixer until the mixture is uniform.

The following mixture is prepared:

| B. | Ben-A-Gel ® EW | 0.55 parts by weight |
| | Distilled water | 72.55 parts by weight |

The resulting mixture is mixed in a propellant type mixer until a smooth gel is formed.

Mixture "B" is added to mixture "A" slowly using a propeller type mixer.

C. Capsules prepared according to Example J (quiacwood oil) are added to the mixture of "B" and "A" using a propellant type mixer (4.00 parts). The capsules are mixed until uniformly dispersed.

The following mixture is prepared:

| D. Sandalwood oil | 2.00 parts by weight |
|---|---|
| Ethanol | 19.8 parts by weight |
| Methyl paraben | 0.2 parts by weight |
| Crodesta ® F-110 | 1.00 parts by weight |

Mixture "D" is mixed at room temperature using a propellant type mixer until the mixture is uniform.

The following mixture is prepared:

| E. SGP Polymer ® 502-S | 0.29 parts by weight |
|---|---|
| Distilled water | 72.71 parts by weight |

The resulting mixture "E" is mixed using a propellant type mixer until a smooth gel is formed.

Mixture "E" is added slowly to mixture "D" using a propeller type mixer.

F. To the mixture of "D" and "E" using a propellant type mixture is added 4.0 parts of the capsules produced according to Example H until the capsules are uniformly dispersed (4.0 parts capsules).

The resulting mixtures of "A", "B", "C" and "D", "E", "F" are then combined to yield a dry cologne powder.

This dry cologne powder is marketed as is or is combined with food grade ethanol at the following rates: 2%, 4%, 6%, 8%, 10%, 12%, 15%, 20%, 25% and 30% in 70%, 80%, 90% and 95% food grade ethanol. On use, (a) as a result of the hydrolytic action of the sweat glands or (b) as a result of the application of mechanical pressure to the particles of entrapped fragrances, yield over a period of 30 hours, a sandalwood/guiacwood fragrance which is evolved from the user.

Figure 10:
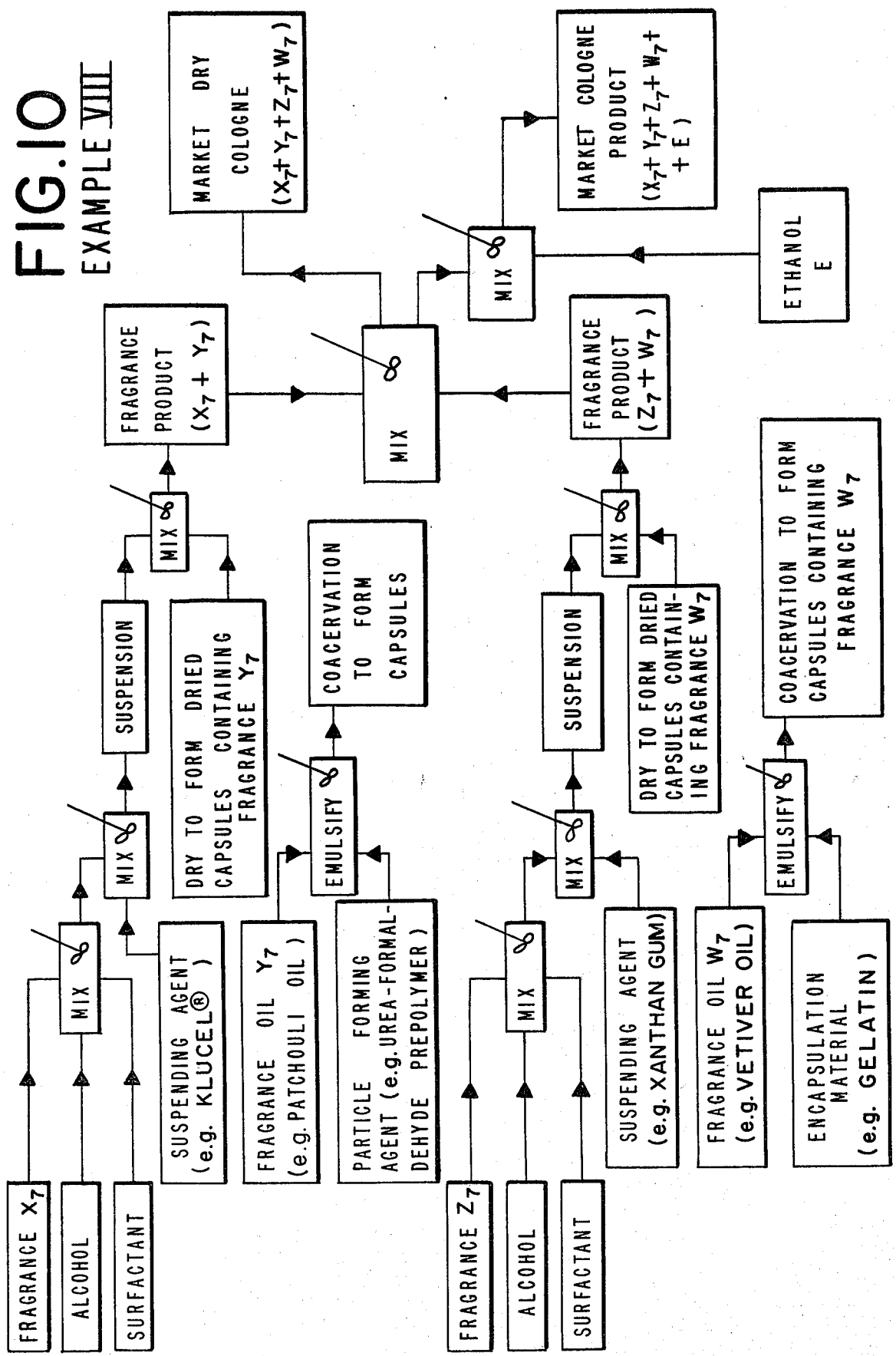
FIG. 10 sets forth a block diagram flow sheet indicating the preparation of the fragranced cologne powder as well as the fragranced cologne liquid of our invention as more fully described in Example VIII wherein, on use, over two different periods of time, two different fragrances are evolved in a controlled manner for a controlled period of time.

FIG. 10 sets forth a block diagram-flow sheet for the process of this example whereby the products denoted as $X_7+Y_7+Z_7+W_7$ and $E+X_7+Y_7+Z_7+W_7$ (liquid cologne) are produced.

EXAMPLE IX

The following mixture is prepared:

| Ingredients | Parts by Weight |
|---|---|
| Fragrance composition of Example A | 48.4 |
| Ethyl cellulose | 3.2 |
| KLUCEL ® GF (brand of hydroxypropyl cellulose manufactured by Hercules Corporation of Wilmington, Delaware having a molecular weight of about 300,000 and a viscosity defined according to FIG. 12) | 9.00 |

The ethyl cellulose and hydroxypropyl cellulose are intimately admixed. The intimate admix of ethyl cellulose and hydroxypropyl cellulose is dispersed in the liquid fragrance composition of Example A with vigorous stirring thereby resulting in a viscous liquid. 48.4 parts by weight of the powder fragrance of Example B is then blended into said viscous liquid with stirring at 25° C. for a period of 30 minutes resulting in a thixatropic sustained release fragrance paste.

This fragrance paste is denoted as fragrance paste $X_8+Y_8$.

The following mixture is prepared:

| Ingredients | Parts by Weight |
|---|---|
| Trans,trans-delta damascone | 20 |
| Propylene glycol | 1.00 |
| KLUCEL ® MF (brand of hydroxypropyl cellulose produced by the Hercules Corporation of Wilmington, Delaware having a molecular weight of about 700,000 and a viscosity defined according to FIG. 2) | 9.00 |

The KLUCEL ® MF is dispersed in the trans,trans-delta damascone with vigorous stirring thereby resulting in a viscous liquid. 65 parts by weight of the powder fragrance composition of Example F (galbanum) is then blended into the viscous liquid with stirring at 25° C. for a period of 30 minutes resulting in a dry, free-flowing sustained release fragrance powder. This fragrance powder is denoted as fragrance powder $Z_8+W_8$. The thixathropic paste $X_8+Y_8$ and the powder $Z_8+W_8$ are then blended in a Banberry Mixer to yield a free-flowing powder denoted as $X_8+Y_8+Z_8+W_8$, a dry cologne product capable of being marketed as such. A portion of the dry cologne product is admixed with ethyl alcohol (food grade 95% aqueous) at the following rates: 2%, 4%, 6%, 8%, 12%, 20%, 30% and 40% in 70%, 80%, 90% and 95% aqueous food grade ethanol. The resulting cologne on use as a result of (a) the hydrolytic action of the body sweat glands or (b) the application of mechanical pressure to the particles of entrapped fragrances, yields a pleasant woody-type fragrance with intense floral, rosy nuances over a period of 36 hours. The resulting fragrance also has the capability of giving rise to an excellent malodor deodorancy effect thereby eliminating malodors and yielding excellent aroma nuances over a long period of time.

Figure 11:
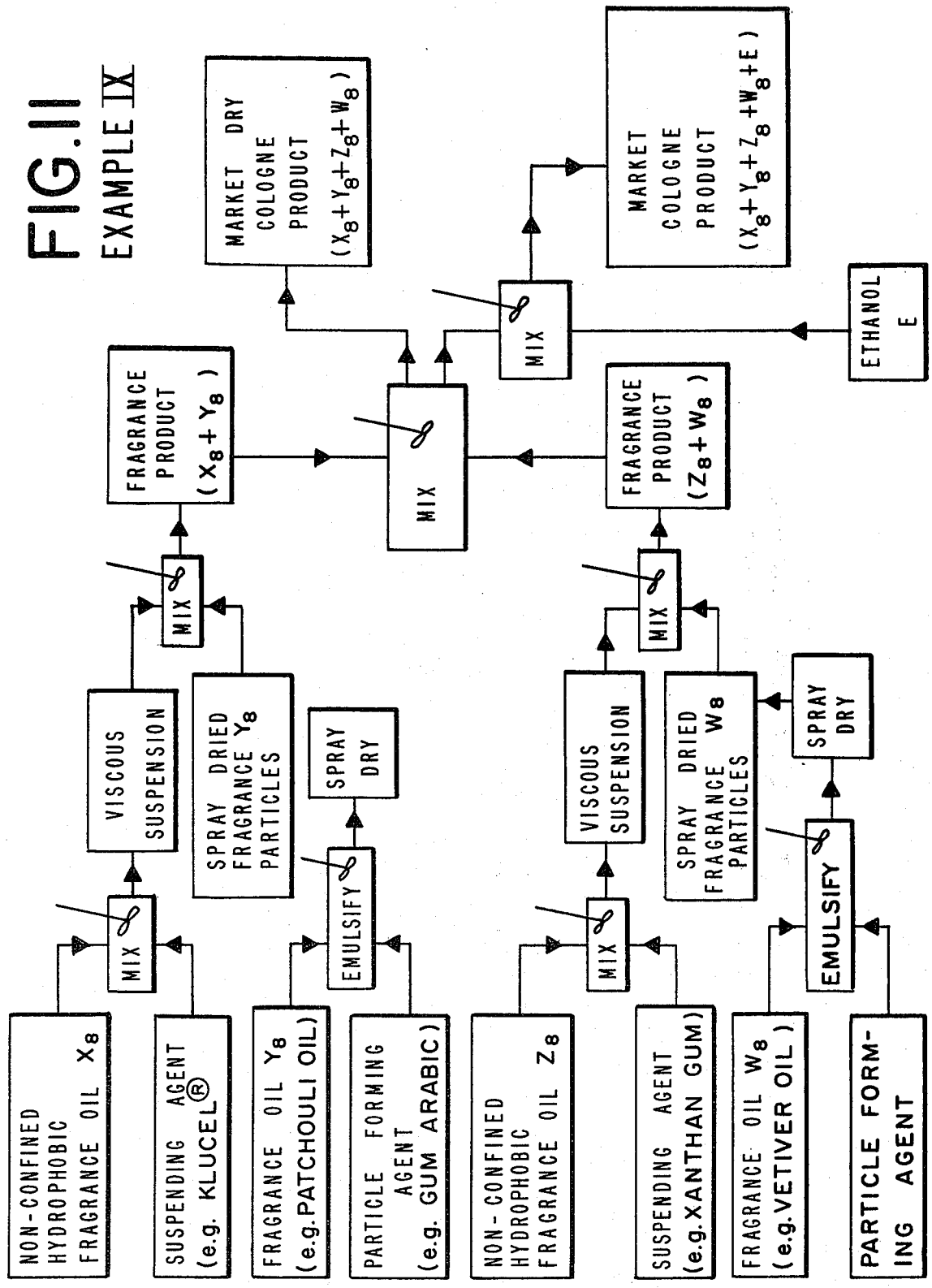
FIG. 11 sets forth a block diagram flow sheet indicating the preparation of the fragranced cologne powder as well as the fragranced cologne liquid of our invention as more fully described in Example IX wherein, on use of the cologne, two different fragrances are evolved over two different periods of time, in a controlled manner.

FIG. 11 sets forth the block diagram-flow sheet for the process of this example.

EXAMPLE X

Trois Côtes Du Force! TM

Dry Powder Cologne and Regular Cologne

The following mixture is prepared:

| A. Guiacwood oil | 2 parts by weight |
|---|---|
| Ethyl alcohol | 19.80 parts by weight |
| Methyl paraben | 0.20 parts by weight |
| Crodesta ® F-110 | 1.00 parts by weight |

The resulting mixture is mixed at room temperature using a propellant type mixer until the mixture is uniform.

The following mixture is prepared:

| B. SGP ® polymer 502-S (prepared according to Example 9 of U.S. Pat. No. 3,935,099 issued on January 27, 1976, the | 0.29 parts by weight |
|---|---|

| | |
|---|---|
| disclosure for which is incorporated herein) | |
| Distilled water | 72.71 parts by weight |

This mixture "B" is mixed using a propellant type mixer at room temperature until a clear gel is formed.

Mixture "B" is added to mixture "A" slowly using a propellant type mixer.

The capsules formed in Example J containing guaicwood oil (4.0 parts) are added to the mixture of "B" and "A" and the resulting mixture "C" is mixed until the capsules are uniformly dispersed using a propellant type mixer at 25° C.

The resulting mixture is herein denoted as mixture "$X_9+Y_9$".

The following mixture $Z_9+W_9$ is prepared:

| Ingredients | Parts by weight |
|---|---|
| Sandalwood oil | 20 |
| Propylene glycol | 1.00 |
| Xanthan gum | 4.00 |
| KLUCEL ® GF (brand of hydroxypropyl cellulose manufactured by the Hercules Corporation of Wilmington, Delaware having a molecular weight of about 300,000 and a viscosity defined according to FIG. 12) | 9.00 |

The KLUCEL®GF is admixed with the xanthan gum and the resulting mixture is dispersed in the sandalwood oil with vigorous stirring thereby resulting in a viscous liquid. 71 parts by weight of the fragrance prepared according to Example H is then blended into the said viscous liquid with stirring at 25° C. for a period of 30 minutes resulting in a dry, free-flowing sustained release fragrance powder denoted as fragrance powder $Z_9+W_9$.

The following mixture is prepared:

| Ingredients | Parts by Weight |
|---|---|
| Rose oil, bulgarian | 47.25 |
| Propylene glycol | 0.50 |
| KLUCEL ® HF (brand of hydroxypropyl cellulose produced by the Hercules Corporation of Wilmington, Delaware having a molecular weight of about 800,000 and a viscosity defined according to FIG. 12) | 5.00 |

The KLUCEL®HF is dispersed in the oil of rose with vigorous stirring thereby resulting in a viscous liquid. 47.25 parts by weight of the fragrance composition prepared according to Example D is then blended into the said viscous liquid with stirring at 25° C. for a period of 30 minutes resulting in a thixatropic sustained release fragrance paste denoted as fragrance product $R_9+S_9$.

Fragrance products $R_9+S_9$, $X_9+Y_9$ and $Z_9+W_9$ are then blended in a mixer at 25° C. for a period of 30 minutes. The resulting product denoted as "$X_9+Y_9+Z_9+W_9+R_9+S_9$" can be marketed as a dry cologne or can be further admixed with ethanol at the following rates: 2%, 4%, 6%, 8%, 10%, 15%, 20%, 30% and 40% in 70%, 80%, 90% and 95% aqueous food grade ethanol to yield the *TROIS CÔTES DUE FORCE!* TM liquid cologne. This liquid cologne exhibits the intensity-time-quality pattern as set forth in FIG. 14 which is a graph of intensity (on a scale of 1–10) vs. time. The fragrance lasts for 25 hours at relatively high intensity.

FIG. 13 is a "block flow diagram" of the process of this example.

EXAMPLE XI

The process of Example X is carried out wherein a cologne solution, $X_9+Y_9+Z_9+W_9+R_9+S_9+E$ is produced. 0.5 parts by weight of an emulsion stabilized prepared according to European patent 28,456 having the structure:

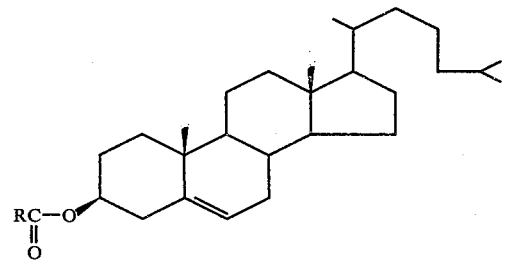

(wherein R represents $C_{15}$ saturated straight chain hydrocarbon) is added together with 4 parts of water. The use of this material is abstracted in published European patent application No. 28,456 thusly:

KAOS* D21 36665 D/21 *EP-28-456
Branched fatty acid cholesterol ester(s) - used as emulsion stabilisers which are not irritating to the skin and can be used in cosmetic and medicinal skin compositions
KAO SOAP KK 31.10.79-JP-139788
B01 E15 (13.05.81) A61k-07/48 C07j-09
30.09.80 as 303436 (34pp1401) (E) CH-669205 FR1442283 3.Jnl.Ref E(AT CH DE FR GB LI)
(A) Branched fatty acid cholesterol esters of formula (I) are new. (R is a satd. 11-23C aliphatic hydrocarbon gp. with at least one alkyl substit. attached to the main chain between the carboxyl bonding position and the centre of the main chain).
(B) Cosmetic compositions contg. a cosmetic oil, water, an emulsifier and (I) are also claimed.
(I) is useful as an emulsion stabiliser esp. for emulsion type cosmetics or medicinal compsns. for application to the skin. (I) is liq. at room temp. and is capable of stabilising an emulsion together with an emulsifier. (I) have very low irritation to the skin and can therefore be used in products which are applied directly to the skin.

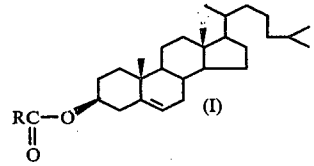

The use of this material gives rise to an improved cologne without any adverse effects upon the length of time that the fragrance is evolved from the user during the use thereof.

In each of the foregoing examples, where SGP ® polymer 502-S is used, it can be replaced at the same level with Carbopol ® resin 907, 910, 941, 934, 934P or 940, acrylic acid polymers manufactured by the B. F. Goodrich Company of 6100 Oak Tree Blvd., Cleveland, Ohio 44131. The molecular weights of these Carbopol ® resins are as follows:

| Type | Molecular Weight |
|---|---|
| 907 | 450,000 |
| 910 | 750,000 |
| 941 | 1,250,000 |
| 934 | 3,000,000 |
| 934P | 3,000,000 |
| 940 | 4,000,000 |

Where used in the preceding examples, supra, Crodesta ®F-110 is sucrose monostearate having the properties set forth supra.

What is claimed is:

1. A cologne comprising particles of a composition consisting essentially of (a) from about 1 up to 10 parts by weight of a non-confined fragrance oil substance selected from the group consisting of non-confined hydrophobic fragrance oils and aqueous emulsions of fragrance oils; (b) from about 2 up to about 10 parts by weight of an entrapped fragrance oil capable of being released hydrolytically or by means of application of mechanical pressure, said fragrance oil being physically entrapped in a particulate material selected from the group consisting of gelatin, dextrin, gum acacia, urea formaldehyde polymers, modified food starch and synthetic polymers capable of being dissolved or decomposed hydrolytically, said solid material having a particle size of from about 3 microns up to about 400 microns, said physically entrapped fragrance oil being organoleptically compatible with said non-confined hydrophobic fragrance oil or fragrance oil emulsion; and (c) from about 0.1 up to about 10 parts by weight of a suspending agent selected from the group consising of hydroxypropyl cellulose having a molecular weight of from about 50,000 up to about 800,000; xanthan gum, ethyl cellulose, silica, suspensions of finely divided clay in water, suspensions of an aqueous fluid-absorbing composition comprising water in soluble alkali salts of aqueous alkali saponified, gelatinized-starch-polyacrylonitrile graft polymers which contain gelatinized starch (GS) and saponified polyacrylonitrile (HPAN) in molar ratios of from about 1:1.5 to about 1:9 GS:HPAN, whereby after the cologne is intimately admixed with ethanol and water a fragrance is released at high fragrance intensity substantially evenly and uniformly over an extended period of time.

2. The cologne of claim 1 wherein the non-confined fragrance is an emulsion consisting essentially of a fragrance oil, ethanol, water, a surfactant and a preservative.

3. The cologne of claim 1 wherein the entrapped fragrance oil is physically entrapped in a poly-2-hydroxyethylmethacrylate polymer having a particle size of from about 200 up to about 400 microns.

4. The cologne of claim 1 wherein the entrapped fragrance oil is physically entrapped in gelatin capsules produced by means of coacervation.

5. The cologne of claim 1 having a plurality of non-confined fragrance oils or fragrance oil emulsions or mixtures thereof and a plurality of chemically different entrapped fragrance oils physically entrapped in solid materials.

6. A process for preparing a cologne comprising (i) admixing (a) from about 1 up to about 10 parts by weight of a non-confined hydrophobic fragrance oil and (b) from about 0.1 up to about 10 parts by weight of a composition of material selected from the group consisting of hydroxypropyl cellulose having a molecular weight of from about 50,000 up to about 800,000; xanthan gum, ethyl cellulose and silica thereby forming a first suspension; and (ii) admixing said first suspension with from about 2 up to about 10 parts by weight of an entrapped fragrance oil, said fragrance oil capable of being released hydrolytically or by means of application of mechanical pressure, said fragrance oil being physically entrapped in a solid material selected from the group consisting of hydrolyzable polymer, gelatin, gum acacia, urea formaldehyde polymers and modified food starch, said solid material having a particle size of from about 3 microns up to about 800 microns thereby forming a second suspension, said physically entrapped fragrance oil being organoleptically compatible with said non-confined hydrophobic fragrance oil.

7. A method for preparing a cologne comprising the steps of (i) admixing from about 2 up to about 10 parts by weight of the combination of a fragrance oil, ethanol, a surfactant and a stabilizer; (ii) admixing water with a finely divided clay or an aqueous fluid-absorbing composition comprising water in soluble alkali salts of aqueous alkali saponified gelatinized starch-polyacrylonitrile graft polymers which contain gelatinized starch (GS) and saponified polyacrylonitrile (HPAN) in molar ratios of from about 1:1.5 up to about 1:9 GS:HPAN to form a second mixture; (iii) admixing said first mixture with said second mixture to form a first suspension; (iv) admixing said first suspension with from about 2 up to about 10 parts by weight of a hydrolytically releasable fragrance oil physically entrapped in a solid material selected from the group consisting of hydrolytically dissolvable or decomposable polymer, urea formaldehyde polymer, gelatin, dextrin, gum acacia and modified food starch, said solid material having a particle size of from about 5 microns up to about 400 microns thereby forming a second suspension, said physically entrapped fragrance oil being organoleptically compatible with said fragrance oil contained in said first mixture.

8. The process of claim 6 comprising the additional step of substantially uniformly distributing the resulting suspension in ethanol and water.

9. The process of claim 7 comprising the additional step of substantially uniformly distributing said second suspension in alcohol and water.

10. The process of claim 7 wherein a plurality of first suspensions having different fragrance oils are formed and admixed with a plurality of non-confined hydrophobic fragrance oils.

11. The process of claim 6 wherein steps (i) and (ii) are repeated using a second hydrophobic fragrance oil chemically different from said first hydrophobic fragrance oil.

12. The process of claim 6 wherein there is admixed a second entrapped fragrance oil which fragrance oil is different in kind from the original entrapped fragrance oil.

13. The process of claim 7 wherein there is admixed a second entrapped fragrance oil which fragrance oil is different in kind from the original entrapped fragrance oil.

14. A cologne comprising particles of a composition consisting essentially of (a) from about 1 up to about 10 parts by weight of a non-confined fragrance oil substance selected from the group consisting of non-confined hydrophobic fragrance oils and aqueous emulsions of fragrance oils; (b) from about 2 up to about 10 parts by weight of an entrapped fragrance oil in particulate form having a particle size of from about 5 microns up to about 400 microns produced by the process which comprises providing a biliquid column comprising an outer stream or jet of capsule shell forming material and a core of fragrance oil to be encapsulated, said column being directed in a trajectory having a horizontal component for a time sufficient for the column to constrict along its length into spheroids of shell forming material, each enclosing a core of fragrance oil and hardening said shell forming material into solid shells encapsulating said fragrance oil within, said encapsulated fragrance oil being organoleptically compatible with said non-confined hydrophobic fragrance oil or fragrance oil emulsions; and (c) from about 0.1 up to about 10 parts by weight of a solid suspending agent.

15. The cologne of claim 14 wherein the solid suspending agent is selected from the group consisting of hydroxypropyl cellulose having a molecular weight of from about 50,000 up to about 800,000; xanthan gum, ethyl cellulose, silica, suspensions of finely divided clay in water, suspensions of an aqueous fluid-absorbing composition comprising water in soluble alkali salts of aqueous alkali saponified, gelatinized-starch-polyacrylonitrile graft polymers which contain gelatinized starch (GS) and saponified polyacrylonitrile (HPAN) in molar ratios of from about 1:1.5 to about 1:9 GS:HPAN, whereby after the cologne is intimately admixed with ethanol and water a fragrance is released at high fragrance intensity substantially evenly and uniformly over an extended period of time.

* * * * *